United States Patent
Huang et al.

(10) Patent No.: US 9,523,682 B2
(45) Date of Patent: Dec. 20, 2016

(54) METHODS AND SYSTEMS FOR DETECTING AN ANALYTE IN A SAMPLE

(71) Applicant: Becton, Dickinson and Company, Franklin Lakes, NJ (US)

(72) Inventors: Wei Huang, Cupertino, CA (US); Scott Bornheimer, Berkeley, CA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 14/237,858

(22) PCT Filed: Nov. 16, 2012

(86) PCT No.: PCT/US2012/065683
§ 371 (c)(1),
(2) Date: Feb. 7, 2014

(87) PCT Pub. No.: WO2013/075031
PCT Pub. Date: May 23, 2013

(65) Prior Publication Data
US 2014/0170642 A1    Jun. 19, 2014

Related U.S. Application Data

(60) Provisional application No. 61/560,752, filed on Nov. 16, 2011.

(51) Int. Cl.
*G01N 33/543* (2006.01)
*G01N 21/64* (2006.01)
(Continued)

(52) U.S. Cl.
CPC ....... *G01N 33/54306* (2013.01); *B01L 3/5027* (2013.01); *G01N 21/6428* (2013.01);
(Continued)

(58) Field of Classification Search
CPC ............. G01N 33/54306; G01N 33/54366; G01N 21/6428; G01N 21/6456; G01N 2035/00158; G01N 21/05; G01N 2021/0346; B01L 3/5027; B01L 2300/0636; B01L 2300/0809; B01L 2300/0838; B01L 2300/087; B01L 2400/0406
See application file for complete search history.

(56) References Cited

U.S. PATENT DOCUMENTS 3,819,913 A    6/1974   Carter et al.
3,916,205 A   10/1975   Kleinerman
(Continued)

FOREIGN PATENT DOCUMENTS

EP    0737855 A1    10/1996
EP    0788615 A1     8/1997
(Continued)

OTHER PUBLICATIONS

Malmstadt et al. Smart mobile affinity matrix for microfluidic immunoassays. Lab Chip 4: 412-415 (2004).*
(Continued)

*Primary Examiner* — Gail R Gabel
(74) *Attorney, Agent, or Firm* — Bret E. Field; Bozicevic, Field & Francis LLP

(57) ABSTRACT

The present disclosure provides methods for the detection of one or more analytes in a sample. Aspects of the methods include flowing a sample (e.g., a biological sample, such as blood) through a channel comprising an analyte specific capture domain stably associated with a surface thereof, wherein the analyte specific capture domain comprises particles displaying a specific binding member for an analyte; and imaging the analyte specific capture domain to detect whether the analyte is present in the sample. Also provided are systems, devices, and kits that may be used in practicing the subject methods. Methods and compositions as described herein find use in a variety of different applications, including diagnostic applications.

15 Claims, 8 Drawing Sheets

(51) Int. Cl.
*B01L 3/00* (2006.01)
*G01N 35/00* (2006.01)
*G01N 21/05* (2006.01)
*G01N 21/03* (2006.01)

(52) U.S. Cl.
CPC ... *G01N 21/6456* (2013.01); *G01N 33/54366* (2013.01); *B01L 2300/0636* (2013.01); *B01L 2300/087* (2013.01); *B01L 2300/0809* (2013.01); *B01L 2300/0838* (2013.01); *B01L 2400/0406* (2013.01); *G01N 21/05* (2013.01); *G01N 2021/0346* (2013.01); *G01N 2035/00158* (2013.01)

(56) References Cited

U.S. PATENT DOCUMENTS

| | | | |
|---|---|---|---|
| 3,963,350 | A | 6/1976 | Watanabe et al. |
| 4,088,448 | A | 5/1978 | Lilja et al. |
| 4,125,828 | A | 11/1978 | Resnick et al. |
| 4,133,873 | A | 1/1979 | Noller |
| 4,337,222 | A | 6/1982 | Kitajima et al. |
| 4,501,496 | A | 2/1985 | Griffin |
| 4,727,020 | A | 2/1988 | Recktenwald |
| 4,751,188 | A | 6/1988 | Valet |
| 4,857,735 | A | 8/1989 | Noller |
| 4,959,305 | A | 9/1990 | Woodrum |
| 5,053,626 | A | 10/1991 | Tillotson |
| 5,073,857 | A | 12/1991 | Peters et al. |
| 5,102,625 | A | 4/1992 | Milo |
| 5,134,662 | A | 7/1992 | Bacus et al. |
| 5,159,642 | A | 10/1992 | Kosaka |
| 5,187,749 | A | 2/1993 | Sugimoto et al. |
| 5,196,709 | A | 3/1993 | Berndt et al. |
| 5,200,152 | A | 4/1993 | Brown |
| 5,294,799 | A | 3/1994 | Aslund et al. |
| 5,332,905 | A | 7/1994 | Brooker et al. |
| 5,348,859 | A | 9/1994 | Brunhouse et al. |
| 5,385,539 | A | 1/1995 | Maynard |
| 5,489,771 | A | 2/1996 | Beach et al. |
| 5,491,343 | A | 2/1996 | Brooker |
| 5,528,045 | A | 6/1996 | Hoffman et al. |
| 5,547,849 | A | 8/1996 | Baer et al. |
| 5,556,764 | A | 9/1996 | Sizto et al. |
| 5,592,291 | A | 1/1997 | Iida |
| 5,599,668 | A | 2/1997 | Stimpson et al. |
| 5,627,037 | A | 5/1997 | Ward et al. |
| 5,661,558 | A | 8/1997 | Nogami et al. |
| 5,674,457 | A | 10/1997 | Williamsson et al. |
| 5,675,155 | A | 10/1997 | Pentoney et al. |
| 5,681,529 | A | 10/1997 | Taguchi et al. |
| 5,692,503 | A | 12/1997 | Kuenstner |
| 5,732,150 | A | 3/1998 | Zhou et al. |
| 5,733,721 | A | 3/1998 | Hemstreet et al. |
| 5,773,301 | A | 6/1998 | Ziegler |
| 5,851,835 | A | 12/1998 | Groner |
| 5,898,487 | A | 4/1999 | Hage |
| 6,043,880 | A | 3/2000 | Andrews et al. |
| 6,064,474 | A | 5/2000 | Lee et al. |
| 6,064,897 | A | 5/2000 | Lindberg et al. |
| 6,094,592 | A | 7/2000 | Yorkey et al. |
| 6,103,197 | A | 8/2000 | Werner |
| 6,154,282 | A | 11/2000 | Lilge et al. |
| 6,159,740 | A | 12/2000 | Hudson et al. |
| 6,181,418 | B1 | 1/2001 | Palumbo et al. |
| 6,187,592 | B1 | 2/2001 | Gourley |
| 6,214,629 | B1 | 4/2001 | Freitag et al. |
| 6,226,347 | B1 | 5/2001 | Golenhofen |
| 6,262,798 | B1 | 7/2001 | Shepherd et al. |
| 6,294,094 | B1 | 9/2001 | Muller et al. |
| 6,305,804 | B1 | 10/2001 | Rice et al. |
| 6,342,376 | B1 | 1/2002 | Kozian et al. |
| 6,345,191 | B1 | 2/2002 | Hartmann et al. |
| 6,350,613 | B1 | 2/2002 | Wardlaw et al. |
| 6,410,341 | B1 | 6/2002 | Freitag et al. |
| 6,453,060 | B1 | 9/2002 | Riley et al. |
| 6,477,394 | B2 | 11/2002 | Rice et al. |
| 6,479,299 | B1 | 11/2002 | Parce et al. |
| 6,493,567 | B1 | 12/2002 | Krivitski et al. |
| 6,519,025 | B2 | 2/2003 | Shepherd et al. |
| 6,563,585 | B1 | 5/2003 | Rao et al. |
| 6,594,075 | B1 | 7/2003 | Kanao |
| 6,611,320 | B1 | 8/2003 | Lindberg et al. |
| 6,612,111 | B1 | 9/2003 | Hodges |
| 6,638,769 | B2 | 10/2003 | Lilja et al. |
| 6,665,060 | B1 | 12/2003 | Zahniser et al. |
| 6,696,240 | B1 | 2/2004 | Kloepfer et al. |
| 6,716,588 | B2 | 4/2004 | Sammak et al. |
| 6,723,290 | B1 | 4/2004 | Wardlaw |
| 6,740,527 | B1 | 5/2004 | Wong et al. |
| 6,825,921 | B1 | 11/2004 | Modlin et al. |
| 6,828,567 | B2 | 12/2004 | Amirkhanian et al. |
| 6,831,733 | B2 | 12/2004 | Pettersson et al. |
| 6,858,400 | B2 | 2/2005 | Bristow |
| 6,862,534 | B2 | 3/2005 | Sterling et al. |
| 6,869,570 | B2 | 3/2005 | Wardlaw |
| 6,898,458 | B2 | 5/2005 | Zeng et al. |
| 6,960,165 | B2 | 11/2005 | Ueno et al. |
| 6,985,224 | B2 | 1/2006 | Hart |
| 6,999,173 | B2 | 2/2006 | Kleinfeld et al. |
| 7,075,628 | B2 | 7/2006 | Shepherd et al. |
| 7,094,562 | B2 | 8/2006 | Bittner |
| 7,096,124 | B2 | 8/2006 | Sterling et al. |
| 7,115,841 | B2 | 10/2006 | Zeng et al. |
| 7,133,545 | B2 | 11/2006 | Douglass et al. |
| 7,146,372 | B2 | 12/2006 | Bacus et al. |
| 7,149,332 | B2 | 12/2006 | Bacus et al. |
| 7,271,912 | B2 | 9/2007 | Sterling et al. |
| 7,279,134 | B2 | 10/2007 | Chan et al. |
| 7,303,922 | B2 | 12/2007 | Jeng et al. |
| 7,319,894 | B2 | 1/2008 | Higgins |
| 7,324,674 | B2 | 1/2008 | Ozawa et al. |
| 7,420,660 | B2 | 9/2008 | Muller |
| 7,426,407 | B2 | 9/2008 | Higgins |
| 7,477,382 | B2 | 1/2009 | Grey et al. |
| 7,515,268 | B1 | 4/2009 | Ayliffe et al. |
| 7,518,727 | B2 | 4/2009 | Pentoney et al. |
| 7,539,335 | B2 | 5/2009 | Fukuyama |
| 7,560,073 | B1 | 7/2009 | Peters et al. |
| 7,625,712 | B2 | 12/2009 | Paul et al. |
| 7,630,063 | B2 | 12/2009 | Padmanabhan et al. |
| 7,674,598 | B2 | 3/2010 | Paul et al. |
| 7,738,094 | B2 | 6/2010 | Goldberg |
| 7,762,946 | B2 | 7/2010 | Sugimoto |
| 7,781,226 | B2 | 8/2010 | McDevitt et al. |
| 7,790,464 | B2 | 9/2010 | Tarasev |
| 7,816,135 | B2 | 10/2010 | Goldberg |
| 7,826,728 | B2 | 11/2010 | Konno et al. |
| 7,854,891 | B2 | 12/2010 | Yamamoto et al. |
| 7,892,551 | B2 | 2/2011 | Glencross |
| 7,903,241 | B2 | 3/2011 | Wardlaw et al. |
| 7,952,692 | B2 | 5/2011 | Primack et al. |
| 8,009,894 | B2 | 8/2011 | Lindberg et al. |
| 8,125,623 | B2 | 2/2012 | Munger et al. |
| 8,224,058 | B2 | 7/2012 | Lindberg et al. |
| 8,244,021 | B2 | 8/2012 | Lett et al. |
| 8,306,594 | B2 | 11/2012 | Paseman et al. |
| 8,353,848 | B2 | 1/2013 | Long et al. |
| 8,377,398 | B2 | 2/2013 | McDevitt et al. |
| 8,406,859 | B2 | 3/2013 | Zuzak et al. |
| 8,483,789 | B2 | 7/2013 | Higgins |
| 8,488,903 | B2 | 7/2013 | Higuchi |
| 8,541,227 | B2 | 9/2013 | Christensen et al. |
| 2003/0152927 | A1 | 8/2003 | Jakobsen et al. |
| 2003/0170613 | A1 | 9/2003 | Straus |
| 2003/0230728 | A1 | 12/2003 | Dai et al. |
| 2004/0224329 | A1* | 11/2004 | Gjerde .............. G01N 1/34 435/6.12 |
| 2005/0142565 | A1 | 6/2005 | Samper et al. |
| 2005/0190058 | A1 | 9/2005 | Call |
| 2006/0024756 | A1 | 2/2006 | Tibbe et al. |
| 2006/0183236 | A1 | 8/2006 | Berlin et al. |
| 2006/0227325 | A1 | 10/2006 | Rulison et al. |
| 2006/0241495 | A1 | 10/2006 | Kurtz |

(56) References Cited

U.S. PATENT DOCUMENTS

| | | |
|---|---|---|
| 2006/0252079 A1 | 11/2006 | Oldham et al. |
| 2007/0132994 A1 | 6/2007 | Kobayashi et al. |
| 2007/0178009 A1 | 8/2007 | Sakaino et al. |
| 2008/0190220 A1 | 8/2008 | Backes et al. |
| 2008/0203319 A1 | 8/2008 | Pentoney et al. |
| 2008/0213823 A1* | 9/2008 | Christensen ......... G01N 15/147 435/39 |
| 2008/0268469 A1 | 10/2008 | Srienc et al. |
| 2009/0075324 A1 | 3/2009 | Pettersson |
| 2009/0181411 A1 | 7/2009 | Battrell et al. |
| 2009/0317806 A1 | 12/2009 | Hasson |
| 2010/0291599 A1 | 11/2010 | Tague, Jr. et al. |
| 2011/0118139 A1* | 5/2011 | Mehta ............... B01L 3/5027 506/9 |
| 2013/0045529 A1 | 2/2013 | Goldberg et al. |
| 2013/0162990 A1 | 6/2013 | Kobayashi et al. |
| 2014/0200154 A1 | 7/2014 | Sugarman et al. |
| 2015/0125882 A1 | 5/2015 | Bornheimer et al. |
| 2015/0132789 A1 | 5/2015 | Bornheimer et al. |

FOREIGN PATENT DOCUMENTS

| | | |
|---|---|---|
| EP | 0821784 B1 | 11/1998 |
| EP | 0959346 A2 | 11/1999 |
| EP | 0663070 B1 | 5/2000 |
| EP | 0681177 B1 | 7/2000 |
| EP | 0744600 B1 | 8/2001 |
| EP | 0818682 B1 | 10/2001 |
| EP | 0809807 B1 | 7/2002 |
| EP | 0800074 B1 | 7/2003 |
| EP | 0969279 B1 | 10/2003 |
| EP | 1347702 A2 | 10/2003 |
| EP | 1456649 B1 | 7/2006 |
| EP | 1701150 A1 | 9/2006 |
| EP | 1324021 B1 | 1/2008 |
| EP | 1924195 A2 | 5/2008 |
| EP | 1990638 A1 | 11/2008 |
| EP | 2041549 | 4/2009 |
| EP | 2083687 A1 | 8/2009 |
| EP | 1405073 B1 | 3/2010 |
| EP | 2232442 A1 | 9/2010 |
| EP | 1698883 B1 | 1/2011 |
| EP | 2016390 B1 | 4/2013 |
| EP | 2605020 A2 | 6/2013 |
| EP | 1558934 B1 | 7/2013 |
| JP | 2000292354 A | 10/2000 |
| JP | 2001-088098 A3 | 4/2001 |
| JP | 2002-506208 A | 2/2002 |
| JP | 2002-516982 | 6/2002 |
| JP | 2006515065 A | 5/2006 |
| WO | WO 99-20998 A1 | 4/1999 |
| WO | WO 99/45384 A1 | 9/1999 |
| WO | 00/29847 A2 | 5/2000 |
| WO | WO 00/28297 A2 | 5/2000 |
| WO | WO 02/44729 A1 | 6/2002 |
| WO | WO 02/50518 A2 | 6/2002 |
| WO | WO 03-036290 A1 | 5/2003 |
| WO | 2004017374 A2 | 2/2004 |
| WO | 2004/100887 A2 | 11/2004 |
| WO | 2005100539 A2 | 10/2005 |
| WO | WO 2006/047831 A1 | 5/2006 |
| WO | WO 2006/096126 A1 | 9/2006 |
| WO | WO 2006/116616 A2 | 11/2006 |
| WO | WO 2006/119368 A2 | 11/2006 |
| WO | WO 2007/012975 A1 | 2/2007 |
| WO | WO 2007/033318 A2 | 3/2007 |
| WO | WO 2007/051861 A2 | 5/2007 |
| WO | WO 2007/111555 A1 | 10/2007 |
| WO | WO 2008/002462 A2 | 1/2008 |
| WO | WO 2008/010761 A1 | 1/2008 |
| WO | WO 2008/037068 A1 | 4/2008 |
| WO | WO 2008-103992 A2 | 8/2008 |
| WO | WO 2009/091318 A1 | 7/2009 |
| WO | WO 2010-085658 A1 | 7/2010 |
| WO | WO 2011-133540 A2 | 10/2011 |
| WO | WO 2013/075031 A1 | 5/2013 |

OTHER PUBLICATIONS

Malmstadt et al. "'Smart' mobile affinity matrix for microfluidic immunoassays," Lab on a Chip 2004, vol. 4, pp. 412-415.

Tsougeni et al. "'Smart' polymeric microfluidics fabricated by plasma processing: controlled wetting, capillary filling and hydrophobic valving," Lab on a Chip 2010, vol. 10, pp. 462-469.

Beach, J. M. "A LED light calibration source for dual-wavelength microscopy," Cell Calcium, 21 (1 ): 63-68 (1997).

Bornheimer et al. "Development of the BD FACSPresto™ System for Point-of-Care Determination of CD4 absolute count %CD4, and total Hb", BD Biosciences IAS FACSPresto Poster (2013), 1 page.

Cheng et al. "A microfluidic device for practical label-free CD4+ T cell counting of HIV- infected subjects," Lab Chip, 7: 170-178 (2007).

Debernardi et al. "Single cell Ca2+ /cAMP cross-talk monitoring by simutaneous Ca2+ /cAMP fluorescence ratio imaging," Proc. Natl. Acad. Sci. 93:4577-4582 (1996).

Fischer et al. "An affordable, portable fluorescent imaging device for skin lesion detection using a dual wavelength approach for image contrast enhancement and aminolaevulinic acid-induced protoporphyrin IX. Part I. Design, spectral and spatial characteristics," Lasers Med Sci., 16: 199-296 (2001).

Fischer et al. "An affordable, portable fluorescent imaging device for skin lesion detection using a dual wavelength approach for image contrast enhancement and aminolaevulinic acid-induced protoporphyrin IX. Part II. In vivo testing," Lasers Med Sci., 16: 207-212 (2001).

Fridley et al. Controlled release of dry reagents in porous media for tunable temporal and spatial distribution upon rehydration, Lab Chip. Nov. 7, 2012;12(21):4321-4327.

Gerstner et al. "Quantitative Histology by Multicolor Slide-based Cytometry," Cytometry Part A, 50A: 210-219 (2004).

Hart et al. "Light emitting diode excitation emission matrix fluorescence spectroscopy," Analyst. (127): 1693-1699 (2002).

Heiden et al. "New Epi-Fluorescence optical system for independent analysis of two different fluorochromes in microscopy," Cytometry 20: 95-101 (1995).

Holland et al. "Point-of-care molecular diagnostic systems—past, present and future," Current Opinion in Microbiology, 8: 504-509 (2005).

Janossy et al. "Precise CD4 T-Cell counting using red diode laser excitation: for richer, for poorer," Cytometry (Clinical Cytometry) 50: 78-85 (2002).

Kassotis et al. "An inexpensive dual-excitation apparatus for fluorescence microscopy," Pfugers Arch., 409:47-51 (1987).

Lewis, Ernest K. et al. "Color-blind fluorescence detection for four-color DNA sequencing"; PNAS; www.pnas.org/cgi/ doi/10/ 1073/pnas.0501606102; (Apr. 12, 2005); vol. 102, No. 5: 5346-5351.

Li et al. "CD4 T lymphocytes enumeration by an easy-to-use single platform Image cytometer for HIV monitoring in resource-constrained settings," Cytometry Part B (Clinical Cytometry) 728: 397-407 (2007).

Myers et al. "Innovations in optical microfluidic technologies for point-of-care diagnostics", Lab on a Chip, vol. 8, pp. 2015-2031 (2008).

Rodriguez et al. "A microchip CD4 counting method for HIV monitoring in resource-poor settings," PLoS Medicine, 2 (7): 0663-0672 (2005).

Shapiro, "Cellular astronomy—a foreseeable future in cytometry," Cytometry Part A, 60A: 115-124 (2004).

Shapiro, "Personal cytometers: Slow flow or no flow,"Cytometry Part A, 69A: 620-630 (2006).

Fukano et al. "Fast dual-excitation radiometry with light-emitting diodes and high-speed liquid crystal shutters," Biochemical and Biophysical Research Communications, 340:250-255 (2006).

(56) References Cited

OTHER PUBLICATIONS

Toner et al. "Blood-on-a-chip," Annu. Rev. Biomed. Eng. 7: 77-103 (2005).
Tsien et al. "Measurement of cytosolic free Ca2+ in individual small cells using fluorescence microscopy with dual excitation wavelengths," Cell Calcium 6:145-157 (1985).
Warner et al. "Multicomponent analysis in clinical chemistry by use of rapid scanning fluorescence spectroscopy," Clin. Chern. 22/9: 1483-1492 (1967).
Wittrup et al. "Fluorescence array detector for large-field quantitative fluorescence cytometry," Cytometry 16: 206-213 (1994).
Yager et al. "Microfluidic diagnostic technologies for global public health," Nature 442: 412-418 (2006).
Ymeti et al. "A single platform image cytometer for resource-poor settings to monitor disease progression in HIV infection," Cytometry Part A 71A: 132-142 (2007).

* cited by examiner

B

METHODS AND SYSTEMS FOR DETECTING AN ANALYTE IN A SAMPLE

CROSS-REFERENCE TO RELATED APPLICATIONS

Pursuant to 35 U.S.C. §119 (e), this application claims priority to the filing date of the U.S. Provisional Patent Application Ser. No. 61/560,752, filed Nov. 16, 2011, the disclosure of which is incorporated herein by reference.

INTRODUCTION

Point-of-care (POC) tests facilitate the diagnosis of diseases, especially in resource-limited settings where health care infrastructure is weak, and access to quality and timely medical care is a challenge. POC tests often offer rapid results, allowing for timely initiation of appropriate therapy. Importantly, POC tests can often be simple enough to be used at the primary care level and in remote settings with little to no laboratory infrastructure. POC tests thus offer certain advantages over other types of assays, such as flow cytometry-based microparticle immunoassays, which provide high accuracy and multiplexing, but are often inappropriate for POC settings due to cumbersome sample preparation and expensive instrumentation.

For example, POC tests facilitate the diagnosis or treatment of HIV/AIDS. In most resource-limited countries, eligibility for antiretroviral therapy for HIV/AIDS is based on a count of CD4+ T-lymphocytes. Traditional CD4 count technologies require that a venous blood sample be processed by a laboratory. After testing positive for HIV infection, patients either provide a blood sample immediately or are referred to another facility if the HIV counseling and testing site does not take blood samples. The blood sample is then sent to a laboratory for processing using, e.g., flow cytometry-based assays. Depending on laboratory capacity, results are typically available between 2 and 14 days after the patient has provided the sample. Patients are asked to return to the clinic to receive their results, after which they may be referred for future HIV care and/or treatment. However, roughly 40% of patients in such settings either do not provide a blood sample or do not return to the clinic to obtain their results. POC tests can facilitate the diagnosis of HIV/AIDS by simplifying the blood collection process and by making the results available while the patient is still in the clinical setting. Further, POC tests may potentially empower such patients to self-test in the privacy of their homes, especially for stigmatized diseases such as HIV/AIDS.

Most POC tests for infectious diseases offer only a single diagnosis per test. Recently, multiplexed POC tests have been developed, such as the Multiplo® POC test (MedMira Inc, NS, Canada). Multiplexed POC tests can, in principle, diagnose multiple infectious diseases, thereby offering the promise of simultaneous detection of conditions (e.g., HIV, hepatitis B and C, syphilis, etc.) with greater convenience for patients and providers. Currently, however, evidence of their performance in real world settings is limited. Rapid diagnosis of multiple infectious diseases from a single sample (e.g., a single fingerstick blood drop) using an inexpensive and facile technology available at the point-of-care would greatly improve global health outcomes.

SUMMARY

The present disclosure provides methods for the detection of one or more analytes in a sample. Aspects of the methods include flowing a sample (e.g., a biological sample, such as blood or blood product) through a channel comprising an analyte specific capture domain stably associated with a surface thereof, wherein the capture domain includes particles displaying a specific binding member for an analyte; and imaging the analyte specific capture domain to detect whether the analyte is present in the sample. Also provided are systems, devices, and kits that may be used in practicing the subject methods. The methods and compositions find use in a variety of different applications, including diagnostic applications, environmental testing applications, etc.

The present disclosure provides methods for detecting whether an analyte is present in a sample, the methods including flowing the sample through a capillary channel comprising an analyte specific capture domain stably associated with an inner surface thereof at a known location, wherein the analyte specific capture domain includes particles displaying a specific binding member for the analyte on a surface thereof; and imaging the analyte specific capture domain to detect whether the analyte is present in the sample. Particles of interest include, but are not limited to, beads (e.g., capture beads displaying a specific binding member for the analyte), antibodies and antigen binding fragments thereof, nucleotide sequences, and the like.

The present disclosure also provides methods for detecting whether a plurality of analytes are present in a sample, such as 2 or more analytes (e.g., about 3 to 5 analytes, about 5 to 8 analytes, about 8 to 12 analytes, etc.). For example, to detect a first and second analyte, the methods may include flowing the sample through a capillary channel comprising first and second analyte specific capture domains stably associated with an inner surface thereof at known locations, wherein the first analyte specific capture domain includes particles displaying a specific binding member for the first analyte on a surface thereof, and wherein the second analyte specific capture domain includes particles displaying a specific binding member for the second analyte on a surface thereof; and imaging the first and second analyte specific capture domains to detect whether the first and second analytes are present in the sample. The first and second binding member domains may be located at different locations within the capillary channel. Such methods may be adapted to detect whether a third, fourth, fifth, etc. analyte is present in a sample by, e.g., adding a third, fourth, fifth, etc. analyte specific capture domain for that analyte.

Embodiments of the present disclosure enable the rapid detection of one or more analytes (e.g., 2 or more, such as 3, 4, 5, etc.) in a sample. Such detection may be qualitative, and/or quantitative. A variety of analytes may be detected by methods of the present disclosure, including analytes of biological and/or non-biological origin (e.g., chemical and/or synthetic analytes). Analytes of interest include, but are not limited to, cells, antibodies, polypeptides, polynucleotides, etc. In certain aspects, an analyte is a biomarker. Accordingly, methods of the present disclosure may facilitate the detection, monitoring, and/or diagnosis of one or more conditions in a subject from a biological sample obtained from the subject. Embodiments of the methods are amenable to POC tests to detect multiple infectious diseases from a single biological sample (e.g., a single fingerstick blood drop), using inexpensive technology.

Aspects of the methods include generating a report indicating a likelihood the subject has one or more condition(s) based on the detection of whether an analyte is present in a sample obtained from a subject. The methods of the present disclosure can include selecting a therapy for the subject based on the likelihood of the condition(s). The methods of the present disclosure can include administering a therapy for the subject based on the likelihood of the condition(s). Where the subject is undergoing therapy, the methods of the present disclosure can include modifying therapy for the subject based on the results of the assay(s).

The methods of the present disclosure may be used with a broad range of sample types, including samples containing organic and/or non-organic material. Organic material may be biological or non-biological in origin. Examples of biological samples of interest include, but are not limited to, blood (e.g., whole blood), saliva, urine, bile fluid, and the like. Such samples may be obtained from an in vitro source (e.g., a suspension of cells from laboratory cells grown in culture) or from an in vivo source (e.g., a mammalian subject, a human subject, etc.). In other aspects, samples contain only non-organic material, such as material that is chemical (e.g., synthetic) in origin. In certain embodiments, a sample contains both organic and non-organic material.

Aspects of methods of the present disclosure include labeling an analyte. Labeling of an analyte may be direct or indirect, as is described more fully herein. In certain aspects, a sample is labeled before the sample is flowed through a capillary channel. Embodiments further include also, or instead, flowing an analyte specific label through the capillary channel after a sample is flowed through the capillary channel. A broad range of labels may be used in practicing the subject methods, with labels of interest including, but not limited to, indocarbocyanine (C3), indodicarbocyanine (C5), Cy3, Cy3.5, Cy5, Cy5.5, Cy7, Texas Red, Pacific Blue, Oregon Green 488, Alexa fluor-355, Alexa Fluor 488, Alexa Fluor 532, Alexa Fluor 546, Alexa Fluor-555, Alexa Fluor 568, Alexa Fluor 594, Alexa Fluor 647, Alexa Fluor 660, Alexa Fluor 680, Alexa Fluor 700, JOE, Lissamine, Rhodamine Green, BODIPY, fluorescein isothiocyanate (FITC), carboxy-fluorescein (FAM), phycoerythrin, rhodamine, dichlororhodamine (dRhodamine), carboxy tetramethylrhodamine (TAMRA), carboxy-X-rhodamine (ROX), LIZ, VIC, NED, PET, SYBR, PicoGreen, RiboGreen, and the like.

The present disclosure also provides devices for detecting whether an analyte is present in a sample. Aspects of the devices include a capillary channel that includes an analyte specific capture domain stably associated with an inner surface thereof at a known location, wherein the analyte specific capture domain includes particles (e.g., capture beads) displaying a specific binding member for the analyte on a surface thereof. Methods of making the devices are also provided. For example, methods are provided for stably associating particles (e.g., capture beads) displaying a specific binding member for an analyte with a surface of a channel (e.g., a plastic capillary channel).

The present disclosure further provides systems for detecting whether an analyte is present in a sample. Aspects of embodiments of systems of the present disclosure include a capillary channel that includes an analyte specific capture domain stably associated with an inner surface thereof at a known location, wherein the analyte specific capture domain includes particles displaying a specific binding member for the analyte on a surface thereof; and an imager configured to obtain an image from the analyte specific capture domain. Imagers of interest include, but are not limited to, microscopes (e.g., a low power microscope), cameras (e.g., a CCD camera), optical scanners, and the like. Systems may include a processor, such as a processor contained in a processing module, configured to output a result of whether the analyte is present in the sample based on the image obtained from the imager.

Also provided by the present disclosure are kits, such as kits that include one or more analyte specific labels, and device comprising a capillary channel that includes an analyte specific capture domain stably associated with an inner surface thereof at a known location, wherein the analyte specific capture domain includes particles displaying a specific binding member for the analyte on a surface thereof (e.g., a device as described above).

These and other aspects will be apparent to the ordinarily skilled artisan upon reviewing the present disclosure.

Since early 1960s, immunoassay has become an essential biological analytical technology that is widely used in clinical diagnostics and life science research. Conventional immunoassay technologies, such as ELISA (Enzyme-Linked ImmunoSorbent Assay), combine the binding specificity of biomolecules such as antibodies, with the sensitivity of labels such as radioisotopes, enzymes and fluorescence labels and provide practical solutions for bioanalysis with low cost. However, these assays typically require a bulk liquid separation (i.e., washing) step to remove unbound label molecules before the final measurement, and are not best suited for higher throughput applications that require a high level of automation, or point-of-care applications that demand a user-friendly and low cost assay procedure. In the last three decades, many non-wash immunoassay technologies have been developed and marketed, including EMIT (Enzyme Multiplied Immunoassay Technique), CEDIA (Clone Enzyme Donor Immunoassay), LOCI (luminescence Oxygen Channeling Assay), TR-FRET (time resolved fluorescence resonance energy transfer) and fluorescence polarization. These technologies require complicated preparation of sensing biomolecules or instrumentation and have limited applications, particularly in point-of-care applications.

To address the unmet needs for multiplexed point-of-care immunoassays suitable for the simultaneous detection of multiple diseases from a small volume of sample such as fingerstick whole blood, we have developed a novel approach combining multiplexed microparticle immunoassays with microfluidic assay design and inexpensive digital imaging/image processing, making an easy-to-manufacture platform for accurate measurement of infectious disease markers in whole blood with no sample preparation. The washing step normally required in conventional ELISA assays is eliminated by specifically measuring the bound fluorescence label molecules on microparticles while reducing the interference from unbound label molecules in the assay solution. Unlike conventional assays, where a combined optical signal is measured from a bulk volume of assay solution with no spatial separation, digital imaging provides detailed two-dimensional information in the sample. With imaging process and computer analysis, optical intensity from each microparticle can be measured specifically in the two-dimensional space. Another aspect of our new approach described herein is the defined height to particle size ratio. With channel height to particle ratio of 50 or less, the interference of sample and unbound fluorescence labels in the third z dimension is limited. In contract to a typical microtiter plate-based ELISA assay set up, where a combined optical signal from label molecules bound on the bottom of a microtiter plate is measured from the top of the plate, through several millimeters of assay solution containing unbound label molecules and other potentially interfering substances, our new approach involves imaging of microparticles with a thin layer of assay fluid, thus enabling the assay to be performed without the need for a washing step. As an example, in an embodiment of our invention, microparticles of 7.5 μm diameter are imaged inside a fluidic channel of 50 µm height, thus dramatically reducing the interfere with from sample solution and eliminate the need for bulk separation (washing) of the assay solution.

BRIEF DESCRIPTION OF THE DRAWINGS

The invention may be best understood from the following detailed description when read in conjunction with the accompanying drawings. Included in the drawings are the following figures.

DETAILED DESCRIPTION

Figure 1:
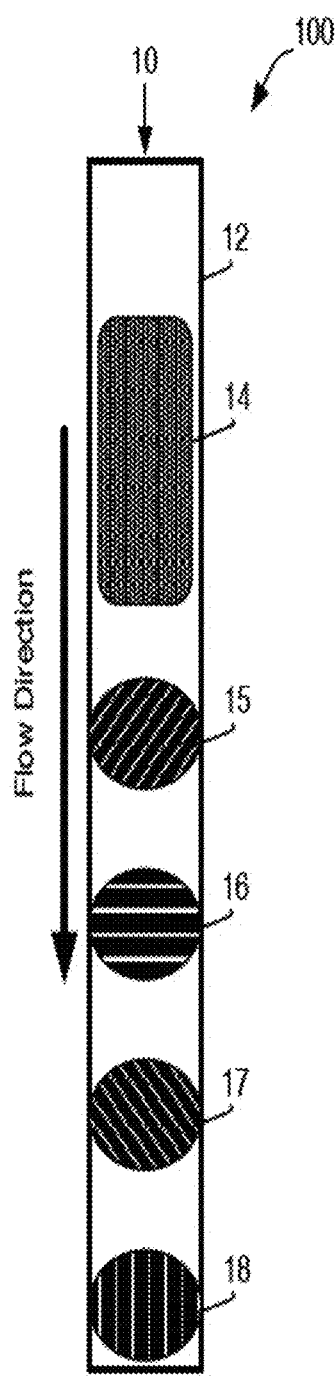
FIG. 1 provides a schematic illustration of certain embodiments of the methods and devices of the present disclosure.

The present disclosure provides methods for the detection of one or more analytes in a sample. Aspects of the methods include flowing a sample (e.g., a biological sample, such as blood or blood product) through a channel comprising an analyte specific capture domain stably associated with a surface thereof, wherein the analyte specific capture domain includes particles displaying a specific binding member for an analyte; and imaging the analyte specific capture domain to detect whether the analyte is present in the sample. Also provided are systems, devices, and kits that may be used in practicing the subject methods.

Before the present invention is described in greater detail, it is to be understood that this invention is not limited to particular embodiments described, as such may vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

Methods

As described above, the present disclosure provides methods for detecting whether an analyte is present in a sample. Aspects of the methods include flowing a sample (e.g., a biological sample, such as blood or blood product) through a channel comprising an analyte specific capture domain stably associated with a surface thereof, wherein the analyte specific capture domain includes particles displaying a specific binding member for an analyte; and imaging the analyte specific capture domain to detect whether the analyte is present in the sample.

Embodiments of the methods include detecting more than one analyte from a single sample, i.e., multiplex analyte detection. Accordingly, the present disclosure provides multiplex assays for identifying a plurality of analytes from a single sample. The subject methods may be used to detect whether 2 or more analytes are present in a sample, including 3 or more, such as about 2 to 100 analytes, e.g., 3 to 5 analytes, 5 to 8 analytes, 8 to 12 analytes, 12 to 15 analytes, 15 to 20 analytes, 20 to 30 analytes, 30 to 40 analytes, 40 to 50 analytes, 50 to 60 analytes, 60 to 70 analytes, 70 to 80 analytes, 80 to 90 analytes, or 90 to 100 analytes. Because assays according to certain embodiments have a spatial component to analyte detection, e.g., they location of the capture domain on the surface of the capillary channel uniquely identifies that analyte for which that capture domain is targeted, a sample may be screened for 100 or more analytes in some instances.

For example, to detect a first and second analyte, the methods may include flowing the sample through a capillary channel that includes first and second analyte specific capture domains stably associated with (e.g., immobilized on) an inner surface thereof at known locations, wherein the first analyte specific capture domain includes particles displaying a specific binding member for the first analyte on a surface thereof, and wherein the second analyte specific capture domain includes particles displaying a specific binding member for the second analyte on a surface thereof; and imaging the first and second analyte specific capture domains to detect whether the first and second analytes are present in the sample. The first and second binding member domains may be located at different locations within the capillary channel. Such methods may be adapted to detect whether a third, fourth, fifth, etc. analyte is present in a sample by, e.g., adding a third, fourth, fifth, etc. analyte specific capture domain for that analyte.

In some embodiments, the methods for detecting whether one or more target analyte(s) are present in a sample may be performed in 3 hours or less, including 60 minutes or less, such as 30 minutes or less, 20 minutes or less, 10 minutes or less, 5 minutes or less, or 1 minute or less. As such, aspects of the methods may be used in POC testing.

In some instances, the assays are "wash-free" assays. By wash free assay is meant that the protocol does not include a washing step between the capture step and imaging step. As such, following sample contact with a capture domain, the capture domain is not washed or otherwise treated to remove sample components prior to imaging. In other words, an image is obtained from the capture domain without first removing any sample components therefrom.

In some embodiments, methods of the invention of detecting whether an analyte is present in a sample are qualitative, where the detection of the analyte is qualitative, e.g., a determination is made that the analyte is or is not present in the sample. In some embodiments, methods of the invention of detecting whether an analyte is present in a sample are quantitative, where the detection of the analyte is quantitative. The methods can include determining a quantitative measure of the number of analyte particles (e.g., antibodies) in a sample. In some embodiments, quantifying the number of analyte particles in a sample includes determining whether the number of analyte particles present is above or below a predetermined threshold.

FIG. 1 provides a schematic illustration of embodiments of the present disclosure. In this embodiment, a sample 10 is introduced into a capillary channel 12. The channel 12 contains a region comprising reagents 14. The reagents in this region may be preserved and/or dried. The sample 10 flows over this region 14, mixing with any reagents that may be present. The sample then flows (e.g., via capillary action) over one or more analyte specific capture domains. In the illustration presented in FIG. 1, the example provides a first analyte specific capture domain 15 for detecting a first analyte, a second analyte specific capture domain 16 for detecting a second analyte, a third analyte specific capture domain 17 for detecting a third analyte, and fourth analyte specific capture domain 18 for detecting a fourth analyte. Each of the analyte specific capture domains 15-18 may be imaged to detect whether the respective analyte is present in the sample 10. In some instances, imaging protocols (as implemented by devices and/or algorithms, may be employed to obtain independent measurements on each bead (of the same assay) which are combined statistically to give an overall result. Accordingly, FIG. 1 illustrates a multiplexed assay.

Figure 2:
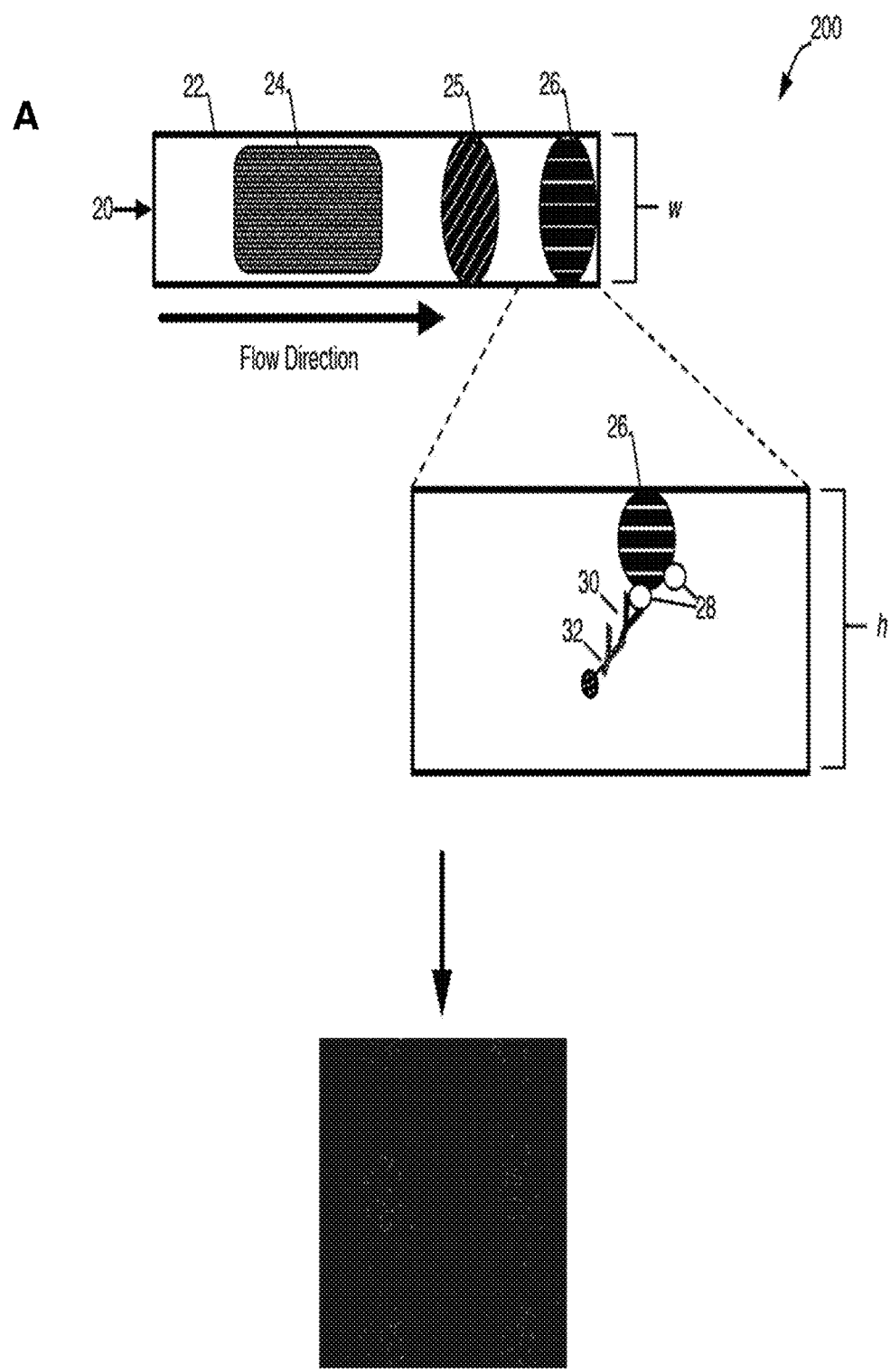
FIG. 2, Panels A-B provide schematic illustrations of embodiments of the present disclosure. Panel A: A schematic illustration of certain embodiments of the methods and devices of the present disclosure, using HIV as an example. Panel B: A schematic illustration of experimental assays described in Examples.
Figure 2:
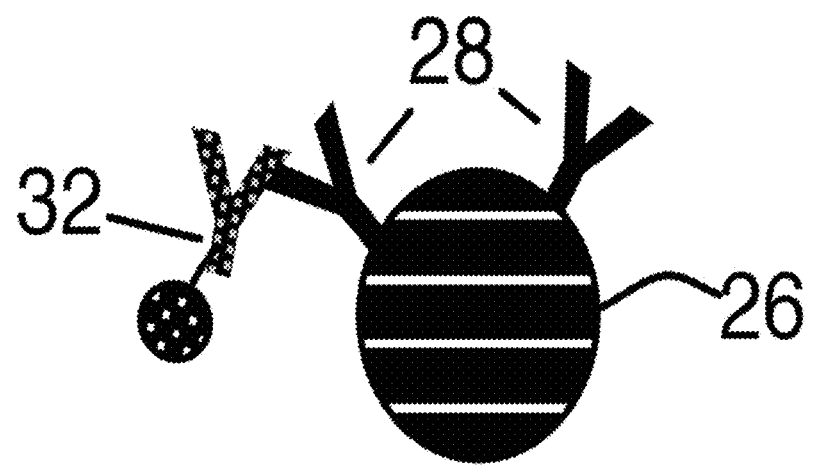

FIG. 2, Panel A provides a schematic illustration of embodiments of the present disclosure. In this non-limiting example 200, a sample 20 (e.g., whole blood) is loaded into a capillary channel 22 of a cartridge device (e.g., as described in greater detail below; see, e.g., FIG. 5), having a width w (e.g., w=3 mm, 5 mm, etc.). The channel 22 is designed such that preserved reagents 24 (e.g., preserved anti-human antibody-allophycocyanine (APC)) are suspended by the introduction of the sample 20, mixed with the sample 20, and then passed into capture domains 25 and 26. The inset shows a close-up side-view of the channel 12 and capture domain 26. The channel 12 has a height h, where h is equal to 50 fold or less greater than the average diameter of the particles contained in capture domain 26. This capture domain 26 contains particles located on the top surface of the channel, e.g., the surface most proximate to the imager. The particles display a binding member 28 (e.g., gp41 antigen) which binds to the target analyte 30 (e.g., anti-gp41 antibody) present in the sample 20. A label 32 (e.g., the preserved anti-human antibody-allophycocyanine (APC)) also binds, resulting in the formation of a complex (e.g., particle/anti-gp41 antibody/APC-anti-human antibody complexes; see, e.g., FIG. 2, Panel B). Imaging of the analyte specific capture domain (bottom image) may be carried out using any convenient protocol (e.g., using a LED, such as a red LED). In certain aspects, imaging is performed without separating the particles from the sample. Imaging may be performed from the top of the channel 22. In imaging, fluorescence may be measured by any convenient protocol to provide a qualitative or quantitative measure, such as by measuring fluorescence by imaging through the top of the cartridge using a low power microscope with a CCD-camera detector and an appropriate filter. Fluorescence intensity on the particles may be quantified after image processing and analysis. For multiplexed assays, particles coated with different disease-associated antigens may be affixed in unique locations in the capillary channel. In this manner, the same label may be used for all capture domains, simplifying the imaging protocol, since the location of the image may be employed to determine the identity of the analyte. Alternatively, two or more capture domains may be present in overlapping locations or the same location of the channel, e.g., where different labels are employed for each analyte or where alternative criteria for bead identification, such as size or intensity in an additional detection channel, are used to have beads from multiple assays in overlapping locations.

Various steps and aspects of the methods shall now be described in greater detail below.

Analytes

As described above, the present disclosure provides methods for detecting whether an analyte is present in a sample. The term "analyte" is used broadly and generically herein to refer to a compound or composition of interest to be detected.

A variety of analytes may be detected by methods of the present disclosure, including analytes of biological and/or non-biological origin (e.g., chemical and/or synthetic analytes). Examples of analytes of interest include, but are not limited to, cells, drugs, hormones, polypeptides, proteins (e.g., antibodies), polysaccharides, nucleic acids, chemicals, heavy metals, pathogens (e.g., bacteria, prion, fungus, virus, etc.), and combinations thereof.

In certain aspects, an analyte is a biomarker. A "biomarker" as used herein generally refers to an organic biomolecule (e.g., an antibody) which is differentially present in a sample taken from a subject of one phenotypic status (e.g., having a disease) as compared with another phenotypic status (e.g., not having the disease or having a different disease). A biomarker is differentially present between different phenotypic statuses if the mean or median level of the biomarker in a first phenotypic status relative to a second phenotypic status is calculated to represent statistically significant differences. Common tests for statistical significance include, among others, t-test, ANOVA, Kruskal-Wallis, Wilcoxon, Mann-Whitney and odds ratio. Biomarkers, alone or in combination, provide measures of relative likelihood that a subject belongs to a phenotypic status of interest. As such, biomarkers can find use as markers for, for example, disease (diagnostics), therapeutic effectiveness of a drug (theranostics), and the like. Biomarkers are thus analytes in assays that facilitate diagnosis, theranostics, and the like.

Biomarkers of interest suitable for identifying one or more conditions (e.g., infectious diseases) include, but are not limited to, those described in, e.g., the Infectious Disease Biomarker Database. This tool is accessible at the website located by placing "www." in front of "biomarker.korea.ac.kr/index.jsp". The Infectious Disease Biomarker Database is described in Yang, et al. (2008) *Nucleic Acid Res.* 36: D455-D460; the disclosure of which is incorporated herein by reference. Suitable biomarkers, as well as specific binding members suitable for use in practicing the subject methods, are further described in, for example, S Aidoo, et al. (2001) *J. Clin. Microbiol.* 39:2572-2575 for HIV; HS Shin, et al. (2001) *Clin. Diagn. Lab. Immunol.* 8:9-13 for hepatitis B; R Allwinn, et al. (1999) *Infection* 27:365-367 for dengue fever; E Araz, et al. (2000) *Trans. R. Soc. Trop. Med. Hyg.* 94:55-56 for malaria; B Berdal, et al. (2000) *Scand. J. Infect. Dis.* 32:287-291 for tularemia; S Chanteau, et al. (2000) *Int. J. Med. Microbiol.* 290:279-283 for bubonic plague; W Ching, et al. (2001) *Clin. Diagn. Lab. Immunol.* 8:409-414 for typhus; J Dominguez, et al. (1999) *Eur. J. Clin. Microbiol. Infect. Dis.* 18:896-898 for Legionellosis; W H Schrier, et al. (1998) *Clin. Chem.* 44:293-298 for *H. pylori* infection; the disclosures of which are incorporated herein by reference.

Samples

Analyte(s) may be detected in a sample. The term "sample" as used herein means any fluid containing one or more individual analytes in suspension at any desired concentration. For example, the sample can contain $10^{11}$ or less, $10^{10}$ or less, $10^9$ or less, $10^8$ or less, $10^7$ or less, $10^6$ or less, $10^5$ or less, $10^4$ or less, $10^3$ or less, 500 or less, 100 or less, 10 or less, or one analyte per milliliter. The sample can contain a known number of analyte molecules or an unknown number of analyte molecules.

In practicing the methods of the present disclosure, the sample can be a biological sample. A "biological sample" encompasses a variety of sample types obtained from a subject. The definition encompasses biological fluids (e.g., blood (including blood fractions (e.g., serum, plasma)); and other liquid samples of biological origin (e.g., saliva, urine, bile fluid). "Blood sample" refers to a biological sample, which is obtained from blood of a subject, and includes whole blood and blood fractions (e.g., plasma or serum) suitable for analysis in the present methods. In general, separation of cellular components and non-cellular components in a blood sample (e.g., by centrifugation) without coagulation provides a blood plasma sample, while such separation of coagulated (clotted) blood provides a blood serum sample. Examples of biological samples of blood include peripheral blood or samples derived from peripheral blood. The definition also includes samples that have been manipulated after their procurement, such as by treatment with reagents, solubilization, or enrichment for certain components, such as one or more polypeptides to be assayed. For example, a biological sample (e.g., blood) can be enriched for a fraction containing an analyte(s) of interest.

Suitable biological samples useful in the methods of the present disclosure include biological fluids (e.g., a blood sample, e.g., whole blood, blood fraction (e.g., serum, plasma)), and other liquid samples of biological origin. Where the biological sample is a blood sample, the blood sample can be obtained from fresh blood or stored blood (e.g. in a blood bank). The biological sample can be a blood sample expressly obtained for an assay of the present disclosure or a blood sample obtained for another purpose which can be subsampled for an assay of the present disclosure.

Samples can be manipulated after procurement, such as by treatment with reagents, solubilization, and/or enrichment for certain components for an analyte(s) to be assayed. Samples can be pretreated as necessary by dilution in an appropriate buffer solution, concentrated if desired, or fractionated by any number of methods including but not limited to ultracentrifugation, fractionation by fast performance liquid chromatography (FPLC), or precipitation.

Accordingly, in some embodiments the sample is obtained from an in vivo source. In certain embodiments the source of the sample is a "mammal" or "mammalian", where these terms are used broadly to describe organisms which are within the class mammalia, including the orders carnivore (e.g., dogs and cats), rodentia (e.g., mice, guinea pigs, and rats), and primates (e.g., humans, chimpanzees, and monkeys). In some instances, the subjects are humans. The methods may be applied to samples obtained from human subjects of both genders and at any stage of development (i.e., neonates, infant, juvenile, adolescent, adult), where in certain embodiments the human subject is a juvenile, adolescent or adult. While the present invention may be applied to samples from a human subject, it is to be understood that the methods may also be carried-out on samples from other animal subjects (that is, in "non-human subjects") such as, but not limited to, birds, mice, rats, dogs, cats, livestock and horses.

In practicing the methods of the present disclosure, the sample can be a non-biological sample. For example, a sample may include a suspension of non-biological particles obtained from, e.g., soil, food, water, and the like. Non-biological samples of interest include samples for use in environmental testing, as described more fully herein.

The sample size itself may also vary. In certain embodiments, a sample includes 100 μl or less of fluid, such as 50 μl or less, including about 5 to 50 μl. A sample may be obtained by, for example, a finger prick (e.g., the sample includes a single fingerstick blood drop). In yet other embodiments, the sample size may be much larger, e.g., 100 μl or greater, such as 500 μl or greater, including 1 ml or greater, e.g., 5 ml or greater, such as where several milliliters of sample are flowed past a capture region to accumulate signal from very low concenrtration anaylte. Any convenient means of acquiring a sample may be used in practicing the subject methods.

Flowing a Sample

In embodiments of the subject methods, a sample is flowed through a channel. The terms "flowing" and "flows" refer to the movement of a sample in any direction, with or without the use of external means (e.g., a pump, syringe, and the like). Examples of flow thus include mechanically-assisted fluid flow, such as flow achieved using a pump, such as a syringe pump, peristaltic pump, or a peristaltic pump. Examples of flow thus also include entirely passive flow, such as gravimetric fluid flow, capillary action, and the like.

The term "capillary action" is used herein to refer to the flow of fluid, either vertically and/or laterally, without the use of external means. Capillary action may occur, e.g., where a fluid is placed in a "capillary channel," which is a channel, pathway, or conduit having properties that permit a fluid to move via capillary action.

For example, samples (e.g., whole blood) may flow via capillary action in channels having dimensions and/or other properties conducive to producing capillary action for that specific sample type. Factors that impact capillary flow include those described in described in, e.g., S Chakraborty (2005) *Lab Chip.* 5(4):421-430. Accordingly, a sample may be flowed through a capillary channel where the fluid is introduced into the channel (e.g., contacted with the channel, injected into the channel, etc.), whereby capillary action causes the fluid to move through the channel.

In certain embodiments, a channel is a "micro" channel. Such channels may have at least one cross-sectional dimension on the order of a millimeter or smaller (e.g., less than or equal to about 1 millimeter). This dimension may be adjusted; in some embodiments the at least one cross-sectional dimension is 500 micrometers or less. In some embodiments, again as applications permit, the cross-sectional dimension is 100 micrometers or less, such as 50 micrometers or less, including 1 micrometer or less).

A cross-sectional dimension is one that is generally perpendicular to the direction of centerline flow, although it should be understood that when encountering flow through elbows or other features that tend to change flow direction, the cross-sectional dimension in play need not be strictly perpendicular to flow. It should also be understood that in some embodiments, a micro-channel may have two or more cross-sectional dimensions such as the height and width of a rectangular cross-section or the major and minor axes of an elliptical cross-section. Either of these dimensions may be compared against sizes presented here. Note that microchannels employed in practicing methods of the present disclosure may have two dimensions that are grossly disproportionate—e.g., a rectangular cross-section having a height of 10 to 200, such as 20 to 100 micrometers and a width on the order of a mm or more, e.g., 3 to 10 mm or more. For example, the channel depicted in FIG. 2, Panel A has a rectangular cross-section having a height of 50 micrometers and a width of 3 mm. Of course, certain devices may employ channels in which the two or more axes are very similar or even identical in size (e.g., channels having a square or circular cross-section).

In view of the above, it should be understood that some of the principles and design features described herein can be scaled to larger devices and systems including devices and systems employing channels reaching the millimeter or even centimeter scale channel cross-sections. Thus, when describing some devices and systems as "micro" it is intended that the description apply equally, in certain embodiments, to some larger scale devices.

The dimensions of a channel may be altered for the particle size(s) used in the analyte specific capture domain(s). In certain aspects, the relative size of the particles and the channel height is such that the channel height and/or width is less than about 50 times the average diameter of the particles, such as about 25-50 times the average diameter of particles, including 5-10 times the average diameter, or 3-5 times the average diameter. For instance, if the particles are beads having an average diameter of about 7.5 μm, in certain embodiments the height and/or width of a channel will be about 375 μm or less, including 75 μm or less, such as 37.5 μm or less (e.g., 22.5 μm).

The cross-sectional dimensions of the channel may be altered for the particular sample type utilized, with the height of the channel such that the sample may separate into one or more layers. For example, where the sample is a biological sample (e.g., blood), red blood cells in the whole blood will settle to the bottom of the channel, leaving clearer plasma at the top. The plasma and red blood cells can thus be passively separated by having suitable height dimension (e.g., about 375 μm or less, including about 37.5 μm or less, such as about 22.5 μm) in the channel. In such aspects, an analyte specific capture domain can be stably associated with a certain surface of the channel so as to preferentially interact with one or more such layers. Using the above example of blood, an analyte specific capture domain that is stably associated with the top surface of a channel would preferentially interact with analyte(s) present in the plasma, while an analyte specific capture domain that is stably associated with the bottom surface of a channel would preferentially interact with analyte(s) present in the red blood cell fraction. Accordingly, by altering the dimensions of a channel and the placement of an analyte specific capture domain (e.g., on the top surface of the channel) potential interference of the detection (e.g., fluorescence detection) from red blood cells is eliminated, allowing a simple assay for whole blood without separation.

The flow rate of a sample through a channel may vary. Where the sample is flowed using strictly passive flow, such as gravimetric fluid flow, capillary action, and the like, the flow rate will be dictated by a number of factors such as the type of sample (e.g., the viscosity), the dimensions of the channel, and the like. In other aspects, flow may be mechanically-assisted (e.g., using a pump, such as a syringe pump, peristaltic pump, or a peristaltic pump) to achieve a desired flow rate (e.g., 0.01 μl/min or greater, 0.1 μl/min or greater, 1 μl/min or greater, 10 μl/min or greater, 100 μl/min or greater, 1 ml/min or greater, or 100 ml/min or greater).

The total time the fluid flows will thus depend on factors such as the flow rate and the length of the channel. In certain aspects, the total flow time is such that the sample has adequate time to mix with one or more reagents that may be present in the channel. Turning again to FIG. 1, for example, the sample 10 flows through the capillary channel 12 by capillary action. The sample 10 passes over a region comprising reagents 14, after which the sample continues to flow (via capillary action) over analyte specific capture domains 15-18. Accordingly, the distance between the region of reagents 14 and the analyte specific capture domains 15-18 may vary depending upon the time desired for the sample to mix with the reagent(s) present.

In certain aspects, a channel may be configured as a flow-through device. By "flow-through" is meant that a sample may enter the channel through an inlet, be carried through the channel, and then exit the channel through an outlet. Aspects of the methods of the present disclosure include collecting the sample that exits from the channel. In certain aspects, the collected sample may be further analyzed (e.g., such as by one or more assays, such as flow cytometry-based assays and the like).

Binding Members

As described above, aspects of the methods include flowing a sample through a channel comprising an analyte specific capture domain stably associated with a surface thereof, wherein the analyte specific capture domain includes particles displaying a specific binding member for an analyte. The term "binding member" as used herein refers to any agent (e.g., a protein (e.g., antibody), small molecule, and the like) that specifically binds to a target analyte. The terms "specific binding," "specifically binds," and the like, refer to the preferential binding to a molecule relative to other molecules or moieties in a solution or reaction mixture. In some embodiments, the affinity between binding member and the target analyte to which it specifically binds when they are specifically bound to each other in a binding complex is characterized by a $K_d$ (dissociation constant) of $10^{-6}$ M or less, such as $10^{-7}$ M or less, including $10^{-8}$ M or less, e.g., $10^{-9}$ M or less, $10^{-10}$ M or less, $10^{-11}$ M or less, $10^{-12}$ M or less, $10^{-13}$ M or less, $10^{-14}$ M or less, including $10^{-15}$ M or less. "Affinity" refers to the strength of binding, increased binding affinity being correlated with a lower $K_d$. As such, "binds specifically" or "specifically binds" is not meant to preclude a given binding member from binding to more than one analyte of interest. For example, antibodies that bind specifically to an analyte polypeptide of interest may be capable of binding other polypeptides at a weak, yet detectable, level (e.g., 10% or less of the binding shown to the polypeptide of interest). Such weak binding, or background binding, is readily discernible from the specific antibody binding to the polypeptide of interest, e.g., by use of appropriate controls.

In certain aspects, the binding members may be antibodies, or antigen-binding fragments thereof. As used herein, the term "antibodies" includes antibodies or immunoglobulins of any isotype, fragments of antibodies which retain specific binding to antigen, including, but not limited to, Fab, Fv, scFv, and Fd fragments, chimeric antibodies, humanized antibodies, single-chain antibodies, and fusion proteins comprising an antigen-binding portion of an antibody and a non-antibody protein. The antibodies may be further conjugated to other moieties, such as members of specific binding pairs, e.g., biotin (member of biotin-avidin specific binding pair), and the like. Also encompassed by the term are Fab', Fv, F(ab')$_2$, and or other antibody fragments that retain specific binding to antigen, and monoclonal antibodies. In other aspects, the binding members may be antigens, where the target analyte(s) are antibodies.

Aspects of embodiments of the methods include binding members that are contained in and/or on particles, such as capture beads (e.g., BD CompBeads, BD Biosciences, San Jose, Calif.). The particles may display a specific binding member (e.g., an antigen) for one or more analytes.

The particles may be any convenient size, and made from any convenient material (e.g., polystyrene beads, latex beads, glass beads, magnetic beads, etc.). In certain aspects, the relative size of the particles and the channel height is adjusted such that the channel height is 50 times or less than the diameter of the particles, such as 5-10 times the diameter of the particles, including 3-5 times the diameter of the particles. Particles may also be naturally occurring particles, e.g., cells or derivatives thereof.

The particles themselves may be located in one or more analyte specific capture domain(s) located within a channel. The analyte specific capture domain(s) may be located at any convenient location(s) in a channel. In some embodiments, the location(s) of the binding member domains are known, while in other embodiments the location(s) are not known. In a given assay, the particles may have the same or different sizes. For example, is some instances particles may have different sizes and or be labeled themselves to increase the number of unique analytes that may be detected in a given assay.

In some instances, the capture domain(s) are located at region which maximizes signal to noise ratio. In certain aspects, analyte specific capture domain(s) are located on the inner surface of the capillary channel that is closest to an imager component, e.g., fluorescent light detector, during use. For example, where the imager is positioned proximal to top outer surface of the channel (where top is relative to the source of gravity), the analyte specific capture domain(s) may be located on a top surface of a channel. Positioning analyte specific capture domain(s) on a top surface of a channel may improve the accuracy of the methods and/or simplify sample preparation, such as by eliminating one or more separation steps. For example, where the sample is a biological sample (e.g., blood), red blood cells in the whole blood will settle to the bottom of the channel, leaving clearer plasma at the top (where top is determined relative to gravitational pull). By placing the analyte specific capture domain(s) on the top surface of the channel and imaging from the top of the channel, potential interference of the detection (e.g., fluorescence detection) from red blood cells is eliminated, allowing a simple assay for whole blood without separation.

The particles may stay localized within the analyte specific capture domain(s) through any suitable means, such as by covalent and/or non-covalent binding between the particles and the channel. For example, stably associating the particles with the channel can be accomplished by methods such as adsorption, absorption, evaporative deposition from a volatile solvent solution, covalent bonding between the particles and the channel, or immunological immobilization. Covalent bonding may, for example, involve bonding the particles to the channel through a coupling agent, such as a cyanogen halide, e.g. cyanogen bromide or by the use of gluteraldehyde, as described in U.S. Pat. No. 4,186,146; the disclosure of which is incorporated herein by reference. Immunological immobilization to the channel may be by absorption, or by covalent linkage, directly, or through a linker of sorts well-known to those skilled in the art. Methods of carrying out these procedures are given, for example, by Iman and Hornby in *Biochemical Journal* (Volume 129; Page 255); Campbell, Hornby, and Morris in *Biochem. Biophys. Acta* (1975), Volume 384; Page 307; Mattisson and Nilsson in *F.E.B.S. Letters*, (1977) Volume 104, Page 78; and in U.S. Pat. Nos. 4,376,110 and 4,452,901; the disclosures of which are incorporated herein by reference.

Methods of interest for stably associating particles of an analyte specific capture domain with surface further include, but are not limited to, methods described in D R Thevenot, et al. *Biosens. Bioelectron.* 16, 121-131 (2001); A F Collings, et al. *Rep. Prog. Phys.* 60, 1397-1445 (1997); Y G Li, et al. *Anal. Chim. Acta* 382, 277-282 (1999); M A Breimer, et al. *Biosens. Bioelectron.* 18, 1135-1147 (2003); X D Dong, et al. *Biolectrochem. Bioenerg.* 42, 63-69 (1997); J T Andersen, et al. *Bioelectrochem. Bioenerg.* 44, 57-63 (1997); F S Ligler, et al. *Anal. Chem.* 74, 713-719 (2002); M. Manning, et al. *Mater. Sci. Eng. C* 23, 347-351 (2003); O A. Sadik, et al. *Anal. Chem.* 74, 3142-3150 (2002); A Akkoyun, et al. *Biosens. Bioelectron.* 17 (8), 655-664 (2002); S Cosnier. *Biosens. Bioelectron.* 14, 443-456 (1999); S. Cosnier, et al. *Electrochim. Acta* 44 (11), 1833-1836 (1999); O Ouerghi, et al. *J. Electroanal. Chem.* 501, 62-69 (2001); J Wang, et al. *Electrochem. Commun.* 5, 83-86 (2003); F Yan, et al. *Anal. Chem.* 73, 5272-5280 (2001); B Hock, et al. *Biosens.*

*Bioelectron.* 17, 239-249 (2002); the disclosures of which are incorporated herein by reference.

In certain aspects, the particles stay localized within the analyte specific capture domain(s) by entirely passive (i.e., non-covalent) interactions between the particles and the channel surface. Such interactions may be strong enough for the particles to remain adhered to the surface of the channel even after fluid flows through the channel (see, e.g., FIG. 3, Panel A). For example, the inner surface may be a plasma etched inner surface and the particles may be stably associated therewith, e.g., as described in the experimental section below, among other locations.

One or more analyte specific capture domains comprising binding members for a target analyte may be present in a channel. For example, in certain aspects one analyte specific capture domain is present for a target analyte. In other aspects, two or more (e.g., 2 to 10, about 10 to 20, etc.) analyte specific capture domains comprising binding members for a target analyte are present. Where two or more analyte specific capture domains are present for a target analyte, the analyte specific capture domains may be homogeneous or heterogeneous (i.e., differing in terms of the binding member for the target analyte, the type of particle used, the size of particle used, etc.)

Where the methods are used to detect whether two or more target analytes are present in a sample, one or more analyte specific capture domain(s) may be present for each target analyte. The analyte specific capture domains for different target analytes can be located in different locations within the channel to enable the multiplexed detection of the different target analytes. For instance, a first analyte specific capture domain for a first analyte may be located in a distinct location from a second analyte specific capture domain for a second analyte, such that imaging of each analyte specific capture domain may detect whether the first or second analyte is present in the sample. Third, fourth, fifth, etc. analyte specific capture domains may be similarly positioned to allow for the detection of third, fourth, fifth, etc. analytes in the sample. See, e.g., FIG. 1.

In certain aspects, particles for first, second, etc. analytes are also, or instead, located in overlapping (including the same) analyte specific capture domains. In such aspects, the particles may display binding members that may be distinguishably labeled for the first, second, etc. analyte. In this manner, the particles can be stably associated with the same or overlapping locations, and nevertheless be distinguished from particles for a different antigen (e.g., distinguished by their fluorescent emissions).

Where desired, a quality control domain may also be present, e.g., a domain having associated therewith particles of known characteristics which provide a signal during imaging which may be employed as a control or reference for assay results.

Labels

In some embodiments, the methods involve the use of a label in detecting whether a target analyte is present in a sample. As used herein, the terms "label" and "detectable label" refer to a molecule capable of detection, including, but not limited to, radioactive isotopes, fluorescers, chemiluminescers, chromophores, enzymes, enzyme substrates, enzyme cofactors, enzyme inhibitors, chromophores, dyes, metal ions, metal sols, ligands (e.g., biotin, avidin, streptavidin or haptens), intercalating dyes and the like. The term "fluorescer" refers to a substance or a portion thereof which is capable of exhibiting fluorescence in the detectable range.

Labels of interest include both directly and indirectly detectable labels. Labels may bind directly to an analyte, and/or to an analyte/binding-member complex (see, e.g., FIG. 2, Panels A-B). FIG. 2, Panel B presents a possible labeling scheme, in which particles 26 displaying binding members 28 (e.g., anti-mouse Ab) bind with a labeled Ab detection reagent 32.

In certain aspects, a sample is labeled before the sample is flowed through a capillary channel. Embodiments further include also, or instead, flowing an analyte specific label through the capillary channel after a sample is flowed through the capillary channel.

In certain aspects, a label may be included within the channel and mixed with the sample as the sample flows through the channel. For example, using the example illustrated in FIG. 1, as the sample 10 flows through the capillary channel 12 by capillary action, the sample 10 passes over a region comprising reagents 14, after which the sample continues to flow (via capillary action) over analyte specific capture domains 15-18. The region comprising reagents 14 may, in some aspects, include one or more labels that are mixed with the sample as it flows through the channel.

Suitable labels for use in the methods described herein include any molecule that is indirectly or directly detectable by spectroscopic, photochemical, biochemical, immunochemical, electrical, optical, chemical, or other means. Labels of interest include, but are not limited to, fluorescein and its derivatives; rhodamine and its derivatives; cyanine and its derivatives; coumarin and its derivatives; Cascade Blue and its derivatives; Lucifer Yellow and its derivatives; BODIPY and its derivatives; and the like. Labels of interest also include fluorophores, such as indocarbocyanine (C3), indodicarbocyanine (C5), Cy3, Cy3.5, Cy5, Cy5.5, Cy7, Texas Red, Pacific Blue, Oregon Green 488, Alexa fluor-355, Alexa Fluor 488, Alexa Fluor 532, Alexa Fluor 546, Alexa Fluor-555, Alexa Fluor 568, Alexa Fluor 594, Alexa Fluor 647, Alexa Fluor 660, Alexa Fluor 680, Alexa Fluor 700, JOE, Lissamine, Rhodamine Green, BODIPY, fluorescein isothiocyanate (FITC), carboxy-fluorescein (FAM), phycoerythrin, rhodamine, dichlororhodamine (dRhodamine), carboxy tetramethylrhodamine (TAMRA), carboxy-X-rhodamine (ROX), LIZ, VIC, NED, PET, SYBR, PicoGreen, RiboGreen, and the like.

Fluorescent labels can be detected using a photodetector to detect emitted light. Suitable detectors include, but are not limited to, detectors as described in U.S. Pat. Nos. 7,927,561 and 7,738,094; the disclosures of which are incorporated herein by reference. Enzymatic labels are typically detected by providing the enzyme with a substrate and detecting the reaction product produced by the action of the enzyme on the substrate, colorimetric labels can be detected by simply visualizing the colored label, and antigenic labels can be detected by providing an antibody (or a binding fragment thereof) that specifically binds to the antigenic label. An antibody that specifically binds to an antigenic label can be directly or indirectly detectable. For example, the antibody can be conjugated to a label moiety (e.g., a fluorophore) that provides the signal (e.g., fluorescence); the antibody can be conjugated to an enzyme (e.g., peroxidase, alkaline phosphatase, etc.) that produces a detectable product (e.g., fluorescent product) when provided with an appropriate substrate (e.g., fluorescent-tyramide, FastRed, etc.); etc.

Where the methods are multiplexed, one or more analytes may be labeled with different labels. In certain aspects, labels are selected so that the labels may be distinguished from one another, such as where the emission spectra of a first label and a second label do not substantially overlap.

Imaging

As described above, embodiments of the methods include imaging the analyte specific capture domain(s) to detect whether the target analyte is present in the sample.

Imaging of the analyte specific capture domain may be carried out using any convenient protocol. The term "imaging" is used broadly to refer to any manner of assessing a region for the presence or absence of a signal from a capture domain, wherein the signal is one produced by the label if the label is present in the capture domain. In other words, when a capture domain is imaged, it is evaluated using any convenient protocol to detect whether a label is present in the domain. In certain aspects, imaging may involve the use of an optical scanner or microscope, such as a low power microscope with a CCD-camera detector and an appropriate filter. In certain aspects, imaging may involve the use of a dedicated imaging device configured for use in methods of the present disclosure (e.g., Alere Pima, BD CD4 Point-of-care, and the like).

Imaging may involve the use of image processing. Any convenient image processing protocol may be applied in methods of the present disclosure. For example, imaging may involve 2D image processing. Such processing may, for instance, involve distinguishing particles from background by size and/or intensity so as to quantify the intensity (e.g., fluorescence intensity) of the particles contained in a specific member binding domain.

In certain aspects, one or more of the above steps may be performed using commercially available imaging software, such as the advanced imaging toolbox from Pipeline Pilot (Accelrys), ImageJ, Matlab, Perkin Elmer Velocity, Media Cybernetics ImagePro Plus, Metamorph, and/or Nikon Elements. In other aspects, one or more steps of the process are performed by custom software modules.

Reports

The present methods may be used to detect one or more biomarkers in a biological sample obtained from a subject. The detection of the biomarker(s) may indicate that the subject has, or is at risk of having, one or more conditions (e.g., HIV, hepatitis B and C, syphilis, malaria, etc.).

The methods of the present disclosure can include generating a report indicating the results of the method and providing guidance as to how the results might be applied to the care of a subject. A "report," as described herein, refers generally to an electronic document or file (e.g., pdf file, monitor display), as well as a tangible document (e.g., paper report). A subject report can be completely or partially electronically generated, e.g., presented on an electronic display (e.g., computer monitor).

The method results in the report can include, for example, one or more of the amount of the target analyte(s) assayed. The level can be reported as a quantitative score (e.g., a concentration, e.g., pg/ml serum) and/or a semi-quantitative score (e.g., a score reflecting an amount of an analyte relative to a control level or a selected threshold level). The method results can optionally include assay results for a control analyte.

Reports can include guidance to a clinician as to a treatment recommendation for the subject based on the likelihood of one or more condition(s) in a subject. For example, reports can include a recommendation regarding further evaluation and/or avoiding expensive and invasive evaluations and/or a recommendations regarding therapeutic intervention (e.g., administering a drug, recommending surgical intervention, etc.), modifying a treatment regimen (e.g., adjusting a drug dose (e.g., increasing or decreasing a dose), adjusting a dosage regimen (e.g., increasing or decreasing dose frequency and/or amount), and the like.

A report can further include one or more of: 1) patient information (e.g., name, medical information (e.g., age, gender, symptoms (e.g., symptoms that may be relevant to diagnosis of the condition(s)), etc.), 2) information about the biological sample (e.g., type, when obtained); 3) information regarding where and how the assay was performed (e.g., testing facility, assay format); 4) service provider information; and/or 5) an interpretive report, which can provide a narrative providing an at least partial interpretation of the results so as to facilitate a diagnosis by a clinician.

Accordingly, the methods disclosed herein can further include a step of generating or outputting a report providing the method results and, optionally, other information such as treatment guidance as described herein. The report can be provided in the form of an electronic medium (e.g., an electronic display on a computer monitor), or in the form of a tangible medium (e.g., a report printed on paper or other tangible medium). An assessment as to the likelihood can be referred to as "risk report" or, simply, a "diagnostic result". The person or entity that prepares a report ("report generator") may also perform steps such as sample gathering, sample processing, and the like. Alternatively, an entity other than the report generator can perform steps such as sample gathering, sample processing, and the like. A report can be provided to a user. A "user" can be, for example, a health professional (e.g., a clinician, a laboratory technician, a physician, etc.).

Devices and Systems

The present disclosure also provides devices and systems for detecting whether an analyte is present in a sample.

Aspects of the devices include a capillary channel that includes an analyte specific capture domain stably associated with an inner surface thereof at a known location, wherein the analyte specific capture domain includes particles (e.g., capture beads) displaying a specific binding member for the analyte on a surface thereof.

As described above, flowing a sample through a channel may involve the use of a "micro" channel that has at least one cross-sectional dimension on the order of a millimeter or smaller (e.g., 1 millimeter or less), where in some embodiments the cross-sectional dimension is 100 micrometers or less (including 50 micrometers or less—such as 1 micrometer or less). Accordingly, in some embodiments, devices of the present disclosure are fabricated using microfabrication technology.

Devices may be made of any convenient material, with a channel comprising glass, plastic, and the like. The devices may be configured to be disposable and/or manufactured for low cost, and may facilitate long term storage (e.g., storage does not require cold-chain storage).

In certain aspects, the devices are configured such that preserved reagents are located in one or more separates location from the particles, and the fluidics are configured such that introduction of the sample re-suspends the reagents, mixes with them, then passes into a detection zone containing the particles. General methods of making such devices include those described in, e.g., U.S. Pat. No. 8,025,850; the disclosure of which is incorporated herein by reference.

Figure 5:
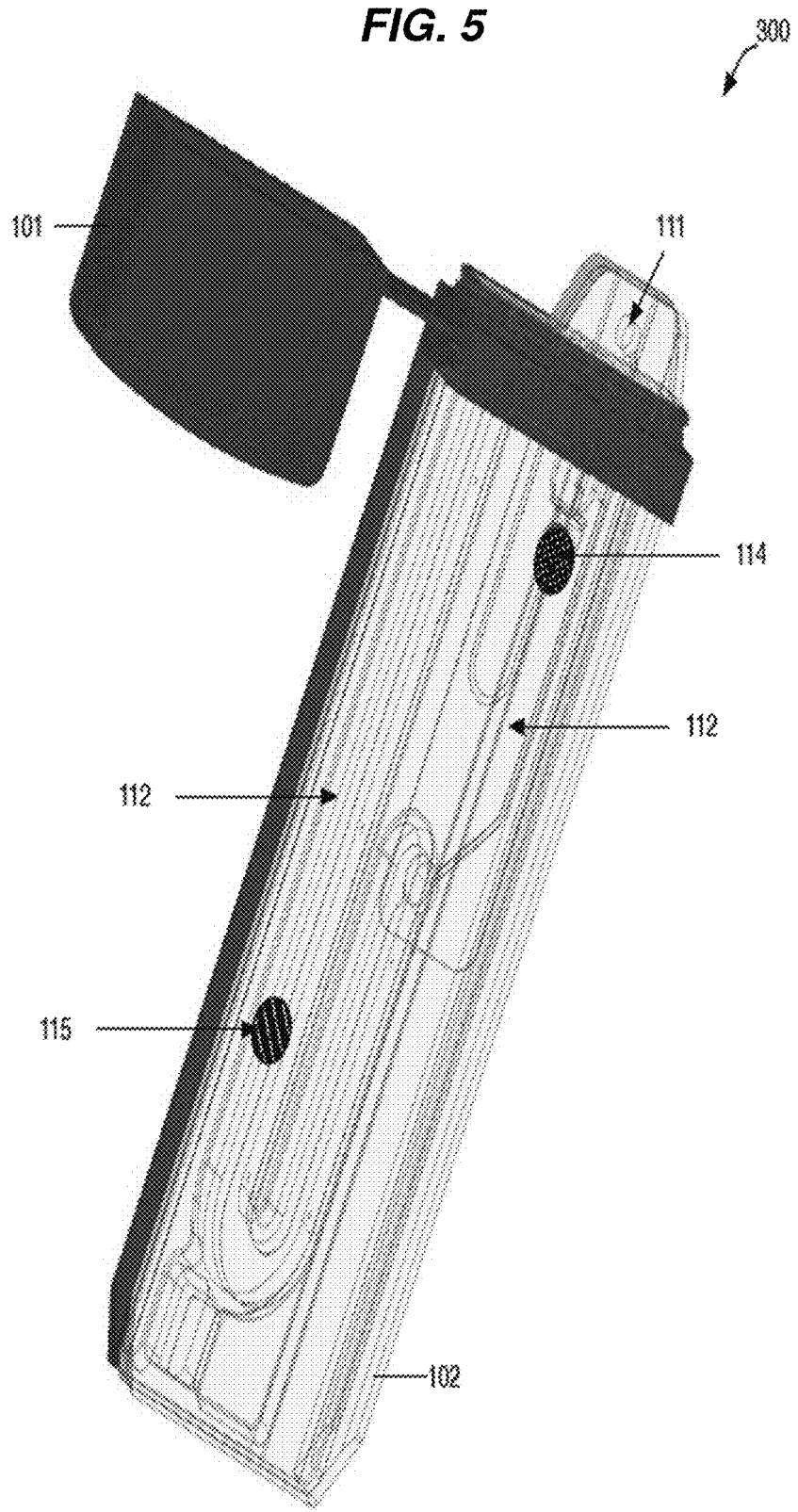
FIG. 5 is an illustration of a cartridge-style device according to an embodiment of the present disclosure.

Devices of interest include cartridge and/or cartridge-style devices. A non-limiting example of such a device is presented in FIG. 5. This device 300 includes a body 102, which includes a top 101. The top 101 may be hinged and/or tethered to the body 102, such that the top 101 may be opened or moved to expose a sample loading area 111. A sample may be loaded into the sample loading area 111, whereby the sample flows into a channel (e.g., a capillary channel) 112 within the body 102. The channel 112 may be straight, curved, and the like. In FIG. 5, for example, the channel 112 includes straight and curved portions. The channel 112 may include a region comprising reagents 114. The reagents in this region may be preserved and/or dried. The sample flows over this region 114, mixing with any reagents that may be present. The sample then flows (e.g., via capillary action) over one or more analyte specific capture domains, such as analyte specific capture domain 115. The analyte specific capture domain 115 may then be imaged to detect whether the target analyte is present in a sample, such as by measuring fluorescence by imaging through the top of the cartridge 300 using a low power microscope with a CCD-camera detector and an appropriate filter.

In the device 300, the sample loading area 111 may include a skin piercing element (e.g., a needle and/or a pin-prick element) to pierce the skin of a subject to produce a sample (e.g., blood). In such embodiments, the sample loading area 111 thus enables the sample to be obtained from the subject, and directly loaded into the device 300 without any additional sample preparation.

The body 102 of the device 300 may be made from any convenient material(s), such as plastic, glass, and the like. In certain aspects, the body 102 is transparent and/or made of a material that permits imaging of the analyte specific capture domains(s) present in the channel 112 through the body 102. The body 102 and top 101 may be configured to be substantially resistant to dust, dirt, water, humidity, temperature, and the like.

The dimensions of such devices may vary. In certain aspects, the length of the device may be 6 inches or less, such as 5 inches, 4 inches, 3 inches, 2 inches or 1 inch. The width of the device may vary, ranging in some aspects from 1 inch or less (e.g., about 0.5 inches to 1.0 inch) to 3 inches or more. In certain aspects, the width is 0.1-0.5 inches, 0.5-1.0 inches, 1.0 to 1.5 inches, 1.5 to 2.0 inches, 2.0 to 2.5 inches, 2.5 to 3.0 inches, or 3.0 to 5.0 inches. The depth (i.e. thickness) of the device may also vary, ranging in certain aspects from 0.1 to 1 inch or more, including about 0.1-0.5 inches, 0.5-1.0 inches, or 1.0 to 1.5 inches.

The shape of the device 300 and/or the body 102 may be configured to be inserted into an imager, such as a port or receptacle in an imager. Accordingly, the shape and/or dimensions of a device may be dictated by the shape and/or dimensions of the port or receptacle of such an imager, or the shape and/or dimensions of the port or receptacle of such an imager may be dictated by the shape and/or dimensions of a device. Insertion of the device into a port or receptacle of an imager may facilitate imaging of one or more analyte specific capture domains in the device, without the circuitry of the imager being directly exposed to the sample contained within the device (e.g., a blood sample).

The present disclosure further provides systems for detecting whether an analyte is present in a sample. Aspects of embodiments of systems of the present disclosure include a capillary channel that includes an analyte specific capture domain stably associated with an inner surface thereof at a known location, wherein the analyte specific capture domain includes particles displaying a specific binding member for the analyte on a surface thereof; and an imager configured to obtain an image from the analyte specific capture domain. Imagers of interest include, but are not limited to, microscopes (e.g., a low power microscope), cameras (e.g., a CCD camera), optical scanners, and the like.

The methods of the present disclosure can be computer-implemented, such that method steps (e.g., assaying, imaging, and the like) are be automated in whole or in part. Accordingly, systems of the present disclosure may include a processing system, which generally includes at least one processor or processing unit or plurality of processors, memory, at least one input device and at least one output device, coupled together via a bus or group of buses. In certain embodiments, an input device and output device can be the same device. The memory can be any form of memory device, for example, volatile or non-volatile memory, solid state storage devices, magnetic devices, etc. The processor can comprise more than one distinct processing device, for example to handle different functions within the processing system.

Systems of the present disclosure may include a number of additional components, such as data output devices, e.g., monitors, printers, and/or speakers, data input devices, e.g., interface ports, a mouse, a keyboard, etc., fluid handling components, power sources, etc.

Kits

Also provided are kits for practicing one or more embodiments of the above-described methods. The subject kits may include various components and reagents, e.g., capillary channel devices (such as cartridge devices); sample preparation reagents, including sample labeling reagents, etc., e.g., as described above.

In some aspects, the kits include one or more analyte specific labels, and a device comprising a capillary channel that includes an analyte specific capture domain stably associated with an inner surface thereof at a known location, wherein the analyte specific capture domain includes particles displaying a specific binding member for the analyte on a surface thereof (e.g., a device as described above).

In some instances, the kits include at least reagents finding use in the methods (e.g., as described above); and a computer readable medium having a computer program stored thereon, wherein the computer program, when loaded into a computer, operates the computer to perform an assay as described herein to detect whether an analyte is present in a sample; and a physical substrate having an address from which to obtain the computer program.

In addition to the above components, the subject kits may further include instructions for practicing the methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium, e.g., CD, DVD, Blu-Ray, flash memory, etc., on which the information has been recorded. Yet another means that may be present is a website address which may be used via the Internet to access the information at a removed site. Any convenient means may be present in the kits.

Utility

The subject methods, devices, systems and kits find use in a variety of different applications where it is desirable to detect whether an analyte is present in a sample.

Diagnostic Testing Applications

For example, the methods, devices, systems, and/or kits of the present disclosure may be used to facilitate the diagnosis of a condition in a subject from a biological sample obtained from the subject. Such methods, devices, systems, and/or kits may be multiplexed, allowing for the rapid diagnosis of multiple conditions (e.g., multiple infectious diseases) from a single sample such as a single fingerstick blood drop. The present disclosure thus facilitates point-of-care detection of one or more biomarkers in a biological sample, thereby providing greater convenience for patients and providers, and improving global health outcomes.

Examples of conditions of interest include, but are not limited to, infectious diseases and/or infections (e.g., viral infections) such as HIV/AIDS, dengue fever, West Nile fever, malaria, Rift Valley fever, ebola, smallpox, Yellow fever, syphilis, and hepatitis B. One or more conditions, such as one or more conditions as listed above, may be amenable to detection and diagnosis in a subject because a number of suitable specific binding members are known, including the specific binding members described in, for example, S Aidoo, et al. (2001) *J. Clin. Microbiol.* 39:2572-2575 for HIV; H S Shin, et al. (2001) *Clin. Diagn. Lab. Immunol.* 8:9-13 for hepatitis B; R Allwinn, et al. (1999) *Infection* 27:365-367 for dengue fever; E Araz, et al. (2000) *Trans. R. Soc. Trop. Med. Hyg.* 94:55-56 for malaria; B Berdal, et al. (2000) *Scand. J. Infect. Dis.* 32:287-291 for tularemia; S Chanteau, et al. (2000) *Int. J. Med. Microbiol.* 290:279-283 for bubonic plague; W Ching, et al. (2001) *Clin. Diagn. Lab. Immunol.* 8:409-414 for typhus; J Dominguez, et al. (1999) *Eur. J. Clin. Microbiol. Infect. Dis.* 18:896-898 for Legionellosis; W H Schrier, et al. (1998) *Clin. Chem.* 44:293-298 for *H. pylori* infection; the disclosures of which are incorporated herein by reference.

For instance, in certain aspects, suitable binding members may be antigens that are specifically bound by antibodies (i.e., the target analytes) against antigens found on the virus capsid. For example, the methods, devices, systems, and/or kits of the present disclosure may be used in the diagnosis of HIV/AIDS, wherein particles contained in one or more analyte specific capture domains display a binding member (e.g., gp41 antigen) which specifically binds to the target analyte (e.g., anti-gp41 antibody) to facilitate a diagnosis of HIV/AIDS.

Accordingly, the methods, devices, systems, and/or kits of the present disclosure can provide results which can then be applied to facilitate decisions as to the care of a subject. Further examples are provided below.

Assay-Guided Therapy and Monitoring of Therapy

The methods of the present disclosure can help a clinician in making a treatment decision for the subject, e.g., whether the results of the method suggest the subject may or may not benefit from antiretroviral therapy for HIV/AIDS. Clinical signs, symptoms and other factors such as family history can also be considered to facilitate selecting a therapy.

The method results can guide a clinician as to whether or not any therapy for treatment of a condition should be administered.

The methods of the present disclosure can facilitate monitoring therapy of a subject undergoing treatment for a condition. For example, where the subject is already receiving a therapy, the method can provide a method of monitoring therapy. In this case, the method results can guide a clinician in adjusting therapy (e.g., whether or not to continue therapy (e.g., so as to avoid relapse), increase or decrease dose, change therapy regimen (e.g., from monotherapy to combination therapy, or from non-surgical therapy to surgical therapy) where the patient is not receiving adequate therapeutic benefit (e.g., the patient is not responding to therapy), and the like). Such methods of monitoring therapy are useful in guiding further treatment decisions, such as whether continued administration of a drug regimen is indicated. The methods of monitoring therapy using the methods of the present disclosure may be used in combination with other methods for assessing whether a subject responds to therapy (is a "responder") or is not exhibiting a sufficient therapeutically beneficial response (is as "nonresponder").

Identifying Subjects for Clinical Trial Populations

The methods of the present disclosure find use in identifying subjects suitable for inclusion or exclusion in a clinical trial based on upon the likelihood the subject has, or is at risk of having, one or more conditions. For example, the methods of the present disclosure can be used to identify subjects suitable for inclusion in a clinical trial (e.g., because they have one or more conditions). In another example, the methods of the present disclosure can be used to identify subjects having one or more conditions so as to exclude such subjects from a clinical trial (e.g., where the clinical trial is to assess efficacy of a drug for a first condition in subjects without a second condition). Methods and devices as described herein may also be employed in the testing of new biomarkers in a clinical trial setting because the POC format decreases the work required of health care practitioners and reduces risks of mistakes; and lowers the complexity of procedure on the patient thus increasing enrollment. Also, by multiplexing tests from the same drop of sample (e.g., fingerstick) multiple clinically relevant outcomes for monitoring or classifying patients can be gotten alongside the new biomarkers under investigation Environmental Testing Applications The methods, devices, systems, and/or kits of the present disclosure may also be used in a number of environmental testing applications, where they may be used to detect analytes such as pesticides, polychlorinated biphenyls (PCBs), heavy metals, endocrine-disrupting chemicals (EDCs), pathogens (e.g., pathogenic bacteria), and the like.

As an example, polychlorinated biphenyls—compounds implicated in producing immunological abnormalities, reproductive dysfunction, and increased thyroid volume—may be detected using methods, devices, systems, and/or kits of the present disclosure in which an anti-PCB antibody is used as the specific binding member. Suitable anti-PCB antibodies are described in, e.g., S Bender, et al. *Environ. Sci. Technol.* 32, 788-797 (1998) and M Masila, et al. *Biotechnol. Bioprocess Eng.* 5, 407-412 (2000); the disclosures of which are incorporated herein by reference.

Similarly, one or more endocrine-disrupting chemicals (EDCs), which structurally resemble endogenous estrogens, may be detected in a sample. EDCs are chemicals that may interfere with the body's endocrine system and produce adverse developmental, reproductive, neurological, and immune effects in human and non-human animals. Suitable specific binding members for use in the detection of EDCs such as alkylphenol ethylates, bisphenol A, and linear alkylbenzene sulphonates are known and described in, e.g., T Matsunaga, et al. *Anal. Chim. Acta* 475, 75-83 (2003); the disclosure of which is incorporated herein by reference.

The methods, devices, systems, and/or kits of the present disclosure may also be used in the detection of pathogens, such as pathogenic bacteria that may be found in soil, food, and marine and estuarine waters. Suitable specific binding members for a number of pathogens, such as *Bacilus globigii*, MS2 bacteriophage, and *Staphlyococcal enterotoxin*, are known and described in, e.g., C A Rowe, et al. *Anal. Chem.* 71, 3846-3852 (1999); the disclosure of which is incorporated herein by reference.

EXEMPLARY EMBODIMENTS

Non-limiting exemplary embodiments of the present disclosure are provided as follows:

1. A method of detecting whether an analyte is present in a sample, the method comprising:
   flowing the sample through a capillary channel comprising an analyte specific capture domain stably associated with an inner surface thereof at a known location, wherein the analyte specific capture domain comprises particles displaying a specific binding member for the analyte on a surface thereof, and wherein the capillary channel has a height less than 50 folds greater than an average diameter of the particles; and
   imaging the analyte specific capture domain to detect whether the analyte is present in the sample, wherein the imaging is performed without separating the particles from the sample.
2. The method according to 1, wherein the detecting is quantitative.
3. The method according to 1, wherein the detecting is semi-quantitative.
4. The method according to 1, wherein the detecting is qualitative.
5. The method according to any of 1-4, wherein the capillary channel has a height less than 40 folds greater than an average diameter of the particles.
6. The method according to any of 1-5, wherein the capillary channel has a height less than 30 folds greater than an average diameter of the particles.
7. The method according to any of 1-6, wherein the capillary channel has a height less than 20 folds greater than an average diameter of the particles.
8. The method according to any of 1-7, wherein the capillary channel has a height less than 10 folds greater than an average diameter of the particles.
9. The method according to any of 1-8, wherein the capillary channel has a height less than 5 folds greater than an average diameter of the particles.
10. The method according to any of 1-9, wherein the capillary channel has a height less than 3 folds greater than an average diameter of the particles.
11. The method according to any of 1-10, comprising labeling the sample before the sample is flowed through the capillary channel.
12. The method according to 11, wherein the label comprises a fluorescent label.
13. The method according to any of 1-12, comprising flowing an analyte specific label through the capillary channel after the sample is flowed through the capillary channel.
14. The method according to 13, wherein the analyte specific label comprises a fluorescent label.
15. The method according to 13 or 14, wherein the analyte specific label comprises an antibody or an antigen binding fragment thereof.
16. The method according to any of 1-15, wherein the particles are capture beads.
17. The method according to 16, wherein the capture beads are coated with a binding reagent that specifically binds to the analyte.
18. The method according to any of 1-17, wherein the sample is a biological sample.
19. The method according to any of 1-18, wherein the biological sample is from a human.
20. The method according to 18 or 19, wherein the biological sample is blood or blood product.
21. The method according to 20, wherein the blood product is serum or plasma.
22. The method according to any of 18-21, comprising obtaining the biological sample from the subject.
23. The method according to any of 1-22, wherein the analyte is an antibody or an antigen binding fragment thereof.
24. The method according to any of 1-23, comprising generating a report indicating a likelihood of a condition based on the detection of whether the analyte is present in the sample.
25. The method according to 24, wherein the condition is selected from the group consisting of HIV, malaria, syphilis, dengue, and diabetes.
26. The method according to 24 or 25, wherein said generating a report is performed by a computer.
27. The method according to 26, wherein the report is displayed to an output device at a location remote to the computer.
28. The method according to any of 1-27, wherein the imaging comprises detecting a fluorescence emission to detect whether the analyte is present in the sample.
29. The method according to any of 1-28, wherein the imaging is performed from a top surface of the channel.
30. The method according to any of 1-29, wherein the imaging is performed from a side surface of the channel.
31. The method according to any of 1-30, wherein the imaging is performed from below the channel.
32. The method according to any of 1-31, wherein the imaging comprises 2D image processing.
33. A method of detecting whether first and second analytes are present in a sample, the method comprising:
   flowing the sample through a capillary channel comprising first and second analyte specific capture domains stably associated with an inner surface thereof at known locations, wherein the first analyte specific capture domain comprises particles displaying a specific binding member for the first analyte on a surface thereof, and wherein the second analyte specific capture domain comprises particles displaying a specific binding member for the second analyte on a surface thereof, wherein the capillary channel has a height less than 50 folds greater than an average diameter of the particles; and
   imaging the first and second analyte specific capture domains to detect whether the first and second analytes are present in the sample.
34. The method according to 33, wherein the imaging is performed without separating the particles from the sample.
35. The method according to 33 or 34, wherein the detecting is quantitative.
36. The method according to 33 or 34, wherein the detecting is semi-quantitative.
37. The method according to 33 or 34, wherein the detecting is qualitative.
38. The method according to any of 33-37, wherein the capillary channel has a height less than 40 folds greater than an average diameter of the particles.
39. The method according to any of 33-38, wherein the capillary channel has a height less than 30 folds greater than an average diameter of the particles.
40. The method according to any of 33-39, wherein the capillary channel has a height less than 20 folds greater than an average diameter of the particles.

41. The method according to any of 33-40, wherein the capillary channel has a height less than 10 folds greater than an average diameter of the particles.
42. The method according to any of 33-41, wherein the capillary channel has a height less than 5 folds greater than an average diameter of the particles.
43. The method according to any of 33-42, wherein the capillary channel has a height less than 3 folds greater than an average diameter of the particles.
44. The method according to any of 33-43, wherein the first and second analyte specific capture domains are located at different positions in the capillary channel.
45. The method according to any of 33-44, further comprising detecting whether a third analyte is present in the sample, wherein the capillary channel comprises a third analyte specific capture domain stably associated with an inner surface thereof at a known location, wherein the third analyte specific capture domain comprises particles displaying a specific binding member for the third analyte on a surface thereof, and imaging the third analyte specific capture domain to detect whether the third analyte is present in the sample.
46. The method according to any of 33-45, comprising labeling the sample before the sample is flowed through the capillary channel.
47. The method according to 46, wherein the label comprises a fluorescent label.
48. The method according to any of 33-47, comprising flowing an analyte specific label through the capillary channel after the sample is flowed through the capillary channel.
49. The method according to 48, wherein the analyte specific label is specific for the first or second analyte.
50. The method according to 48 or 49, wherein the analyte specific label comprises a fluorescent label.
51. The method according to any of 48-50, wherein the analyte specific label comprises an antibody or an antigen binding fragment thereof.
52. The method according to any of 33-51, wherein the particles are capture beads.
53. The method according to 52, wherein the capture beads are coated with a binding reagent that specifically binds to the first or second analyte.
54. The method according to any of 33-53, wherein the sample is a biological sample.
55. The method according to any of 33-54, wherein the biological sample is from a human.
56. The method according to 54 or 55, wherein the biological sample is blood or blood product.
57. The method according to 56, wherein the blood product is serum or plasma.
58. The method according to any of 54-57, comprising obtaining the biological sample from the subject.
59. The method according to any of 33-58, wherein the first analyte is an antibody or an antigen binding fragment thereof.
60. The method according to any of 33-59, wherein the second analyte is an antibody or an antigen binding fragment thereof.
61. The method according to any of 33-60, comprising generating a report indicating a likelihood of a condition based on the detection of whether the first analyte is present in the sample.
62. The method according to 61, wherein the condition is selected from the group consisting of HIV, malaria, syphilis, dengue, and diabetes.
63. The method according to 61 or 62, comprising generating a report indicating a likelihood of a second condition based on the detection of whether the second analyte is present in the sample.
64. The method according to 63, wherein the second condition is selected from the group consisting of HIV, malaria, syphilis, dengue, and diabetes.
65. The method according to any of 61-64, wherein said generating a report is performed by a computer.
66. The method according to 65, wherein the report is displayed to an output device at a location remote to the computer.
67. The method according to any of 33-66, wherein the imaging comprises detecting a fluorescence emission to detect whether the first and second analytes are present in the sample.
68. The method according to any of 33-67, wherein the imaging is performed from a top surface of the channel.
69. The method according to any of 33-68, wherein the imaging is performed from a side surface of the channel.
70. The method according to any of 33-69, wherein the imaging is performed from below the channel.
71. The method according to any of 33-70, wherein the imaging comprises 2D image processing.
72. A system for detecting whether an analyte is present in a sample, the system comprising:
    a capillary channel that comprises an analyte specific capture domain stably associated with an inner surface thereof at a known location, wherein the analyte specific capture domain comprises particles displaying a specific binding member for the analyte on a surface thereof and wherein the capillary channel has a height less than 50 folds greater than an average diameter of the particles; and
    an imager configured to obtain an image from the analyte specific capture domain.
73. The system according to 72, wherein the system further comprises a processing module configured to output a result of whether the analyte is present in the sample based on the image obtained from the imager.
74. The system according to 72 or 73, wherein the capillary channel comprises a second analyte specific capture domain stably associated with an inner surface thereof at a known location, wherein the second analyte specific capture domain comprises particles displaying a specific binding member for a second analyte on a surface thereof, and wherein the imager is configured to obtain an image from the second analyte specific capture domain.
75. The system according to 74, wherein the system further comprises a processing module configured to output a result of whether the second analyte is present in the sample based on the image obtained from the imager.
76. The system according to any of 72-75, wherein the capillary channel is removable.
77. The system according to any of 72-76, wherein the imager is an optical scanner or microscope.
78. The system according to any of 72-77, comprising a counter configured to quantify an amount of analyte from the analyte specific capture domain.
79. A device for detecting whether an analyte is present in a sample, the device comprising:
    a capillary channel that comprises an analyte specific capture domain stably associated with an inner surface thereof at a known location, wherein the analyte specific capture domain comprises particles displaying a specific binding member for the analyte on a surface thereof and wherein the capillary channel has a height less than 50 folds greater than an average diameter of the particles.

80. The device according to 79, wherein the capillary channel has a height less than 40 folds greater than an average diameter of the particles.
81. The device according to any of 79-80, wherein the capillary channel has a height less than 30 folds greater than an average diameter of the particles.
82. The device according to any of 79-81, wherein the capillary channel has a height less than 20 folds greater than an average diameter of the particles.
83. The device according to any of 79-82, wherein the capillary channel has a height less than 10 folds greater than an average diameter of the particles.
84. The device according to any of 79-83, wherein the capillary channel has a height less than 5 folds greater than an average diameter of the particles.
85. The device according to any of 79-84, wherein the capillary channel has a height less than 3 folds greater than an average diameter of the particles.
86. The device according to any of 79-85, wherein the particles are capture beads.
87. The device according to any of 79-86, wherein the capillary channel is plastic.
88. A method of stably associating capture beads displaying a specific binding member for an analyte with an inner surface of a capillary channel, the method comprising: treating the surface of the capillary channel with oxygen plasma to produce a plasma etched surface; and depositing the capture beads on the plasma etched surface.
89. A kit comprising:
   a capillary channel that comprises an analyte specific capture domain stably associated with an inner surface thereof at a known location, wherein the analyte specific capture domain comprises particles displaying a specific binding member for the analyte on a surface thereof and wherein the capillary channel has a height less than 50 folds greater than an average diameter of the particles; and
   an analyte specific label.

EXAMPLES

As can be appreciated from the disclosure provided above, the present disclosure has a wide variety of applications. Accordingly, the following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Those of skill in the art will readily recognize a variety of noncritical parameters that could be changed or modified to yield essentially similar results. Thus, the following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, dimensions, etc.) but some experimental errors and deviations should be accounted for.

Example 1

Stably Associating Capture Beads with a Plastic Capillary Chamber

Capture beads coated with anti-mouse antibodies (BD CompBeads, BD Biosciences, San Jose, Calif.) were stably associated with a surface of a custom molded cycloolefin polymer plastic capillary chamber. To test the impact of bead properties, buffer properties, and capillary chamber surface chemistry on the ability of beads to adhere to the surface after fluid flows into the cartridge, a series of tests were performed.

The impact of the surface chemistry on the ability of the beads to adhere to a plastic surface under the given conditions was tested by attaching BD TruCount™ beads on plastic surfaces and flowing human plasma through the surface. Beads were imaged using a custom-built digital imaging system. The effect of bead properties on the ability of the capture beads to adhere to a plastic capillary chamber surface is depicted in FIG. 3, Panel B.

Figure 3:
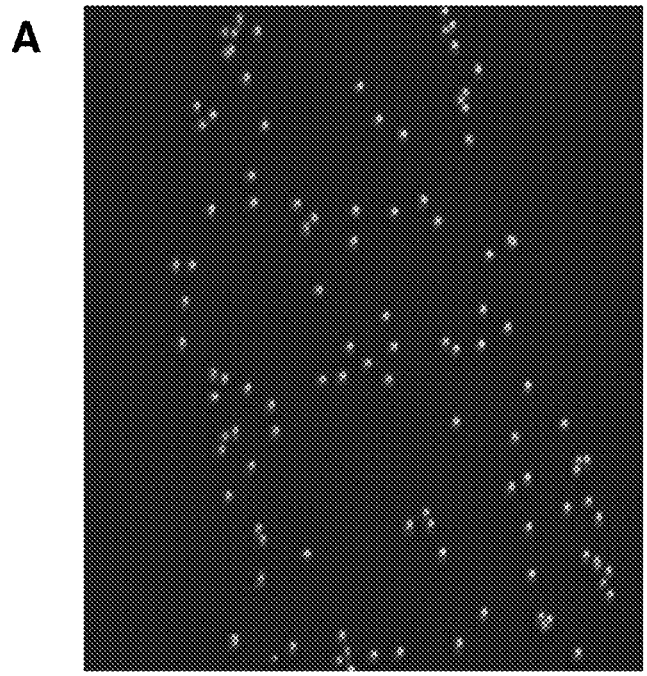
FIG. 3, Panels A-B provide images showing the effects of device surface chemistry on the ability of beads to adhere to the surface of a capillary channel after fluid flows into the cartridge. Panel A: BD TruCount™ Beads adhere to the capillary channel of a plastic device where the device surface was treated with Oxygen plasma. Panel B: Beads lose adherence on cartridge surface that was not treated with Oxygen plasma, and are washed away. Arrows indicate capture beads that have been moved as a result of fluid flowing through the capillary channel via capillary action.
Figure 3:
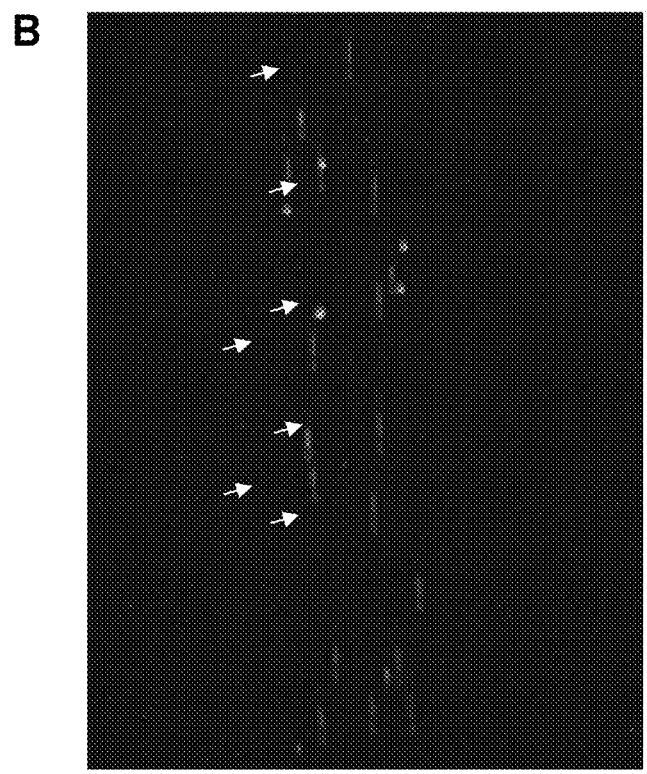

The effect of capillary chamber surface chemistry on the ability of the capture beads to adhere to a plastic capillary chamber surface is depicted in FIG. 3, Panel B. In contrast, cartridge surface treated with oxygen plasma allows beads to adhere to the cartridge surface (FIG. 3, Panel A).

Example 2

Detection of an Analyte in a Sample

A general schematic overview of the below experiments are presented in FIG. 2, Panels A-B. Capture beads (BD CompBeads, BD Biosciences, San Jose, Calif.) were stably associated with the upper surface of a capillary chamber, as described above in Example 1. The beads were coated with anti-mouse antibodies, such that the beads would capture any mouse antibodies in the sample. The beads were labeled with mouse anti-human antibody immobilized in a spot on the upper surface of the capillary chamber. The beads stayed localized in the spot by inherent, presumably passive, interactions between the beads and the plastic chamber surface.

The capillary channel was designed such that the channel height was less than about 10 times the diameter of the capture beads, with ideal performance observed when the channel height was about 3-5 times the diameter of the capture beads.

At such dimensions, the relative low channel height reduced the background fluorescence signal and better allowed the fluorescence signal from the capture beads to be measured with a CCD camera, such as a CCD camera incorporated into an imaging device as described in U.S. Pat. Nos. 7,927,561 and 7,738,094; the disclosures of which are each incorporated herein by reference. The capillary channel was made of plastic.

Three differently labeled populations of mouse antibody, labeled with APC, PE-Cy5, and PE, respectively, were added to a human whole blood sample. 20 μL of the human whole blood was then introduced into the capillary channel. The sample was allowed to move down the capillary by capillary action to the spot of immobilized capture beads, allowing capture of the labeled antibodies.

Figure 4:
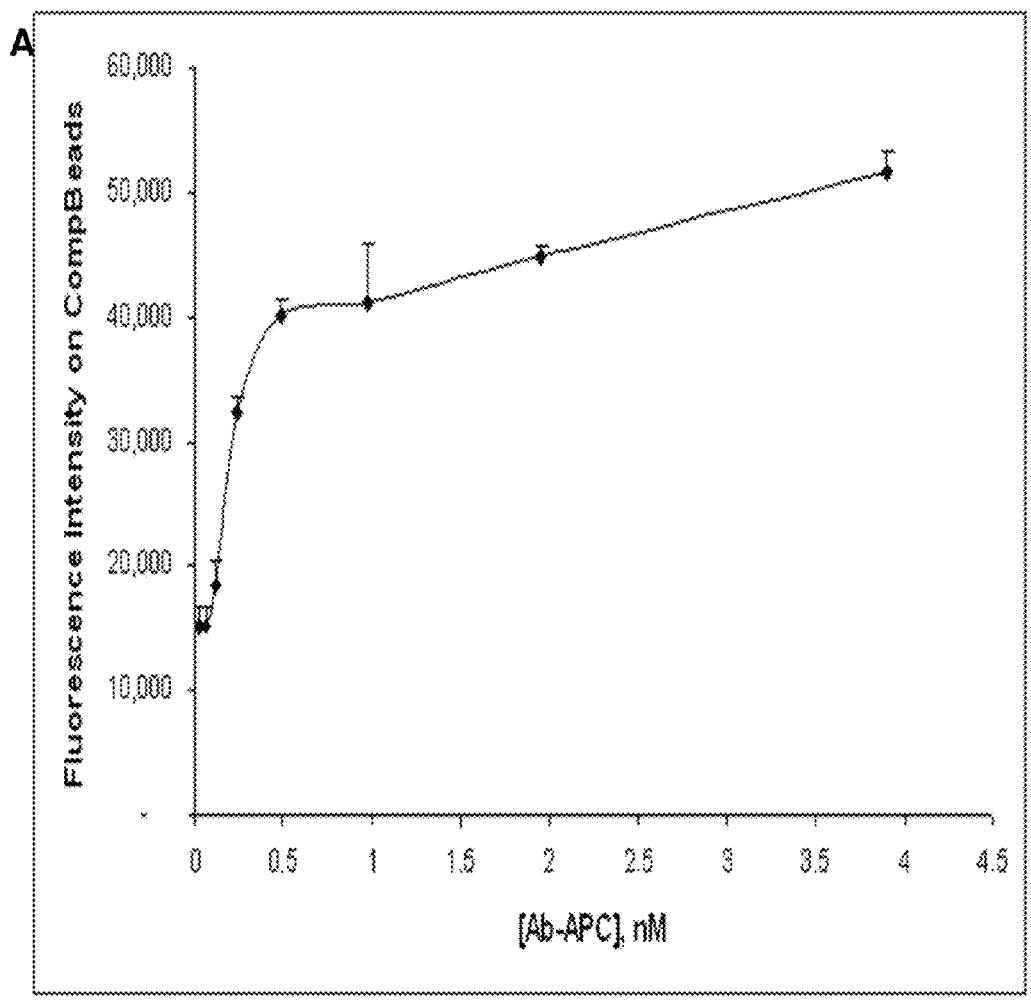
FIG. 4, Panels A-C provide data obtained from the detection of labeled mouse antibodies in whole blood with immobilized BD CompBeads (coated with anti-mouse Ab), using methods and devices of the present disclosure. Error bars represent the standard deviation of 3 replicates (FOVs) in a single channel. Panels A-C show the detection of mouse antibodies labeled with APC, PE-Cy5, and PE, respectively.
Figure 4:
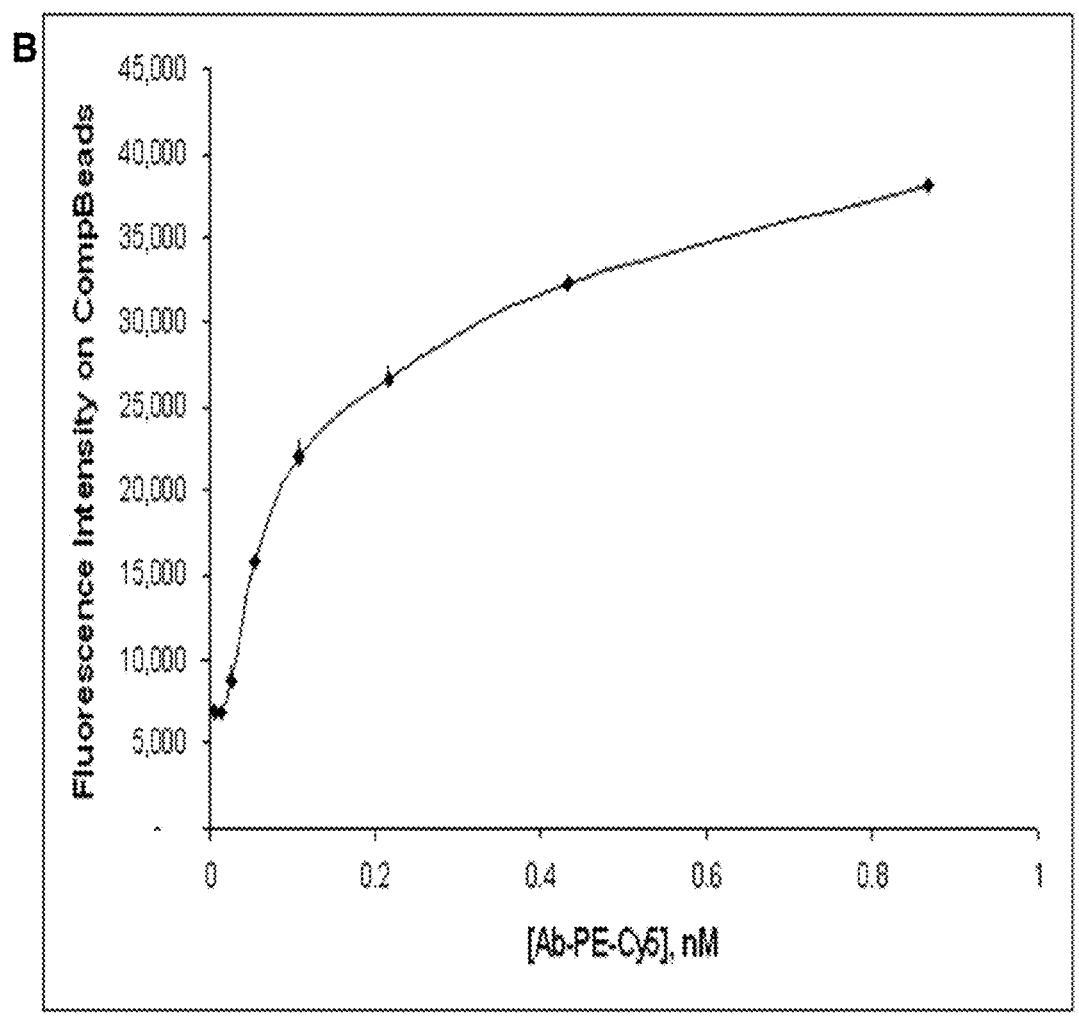
Figure 4:
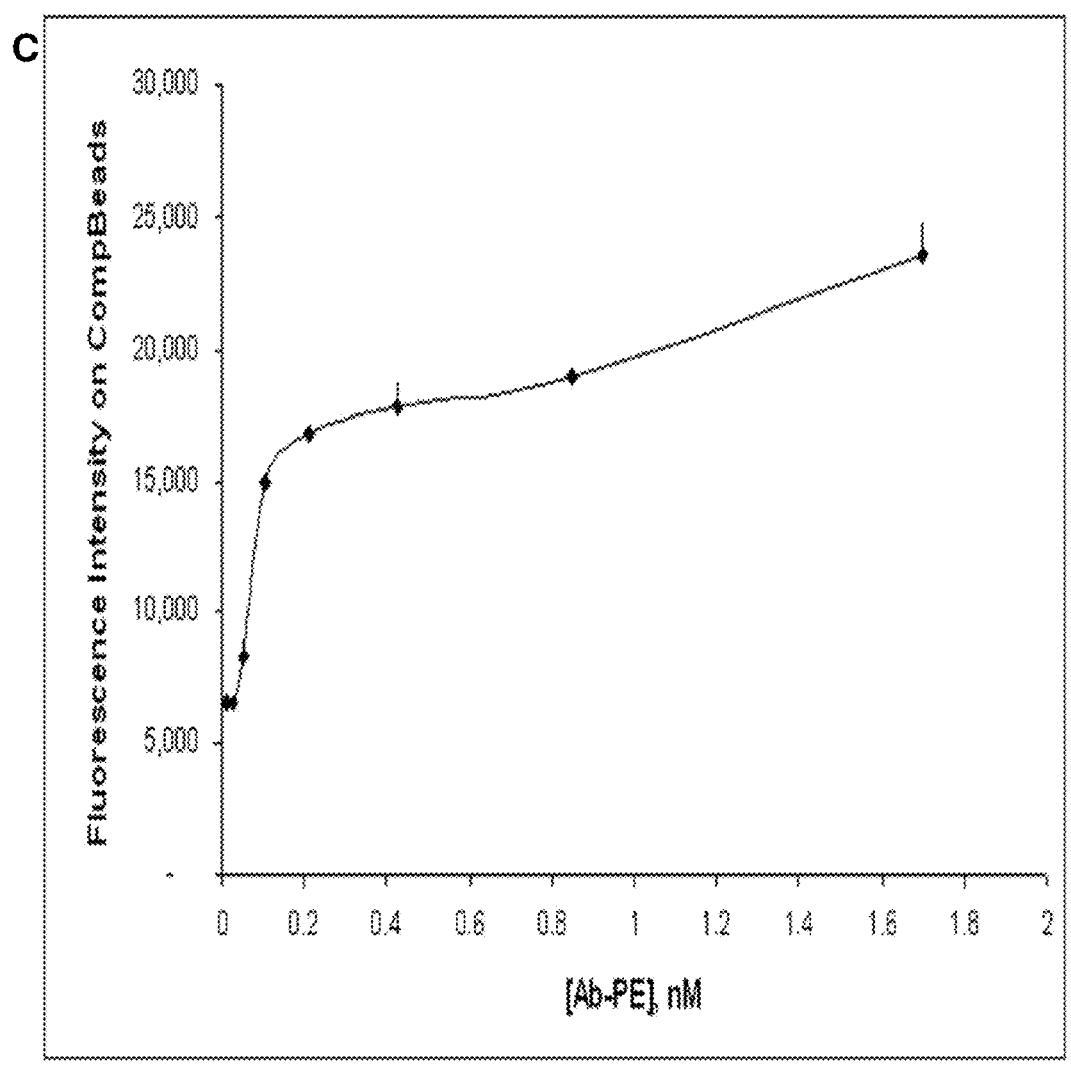

The fluorescence of the captured and labeled antibodies was then measured using a low power microscope. Filters were used to separate the light from the three dyes used, thus enabling independent measurements of the fluorescence. The results, shown in FIG. 4, Panels A-C, show that fluorescent readouts for each of the dyes were easily detectable using a low power microscope.

Although the foregoing invention has been described in some detail by way of illustration and example for purposes of clarity of understanding, it is readily apparent to those of ordinary skill in the art in light of the teachings of this disclosure that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A method of detecting whether an analyte is present in a sample, the method comprising:
   (a) contacting a sample with a fluorescent label that specifically binds to the analyte to produce a fluorescently labelled sample;
   (b) flowing the fluorescently labelled sample through a capillary channel of a cartridge device comprising a first analyte specific capture domain on an inner surface of the capillary channel at a known location, wherein the first analyte specific capture domain comprises:
      (i) particles adhered to the surface of the capillary channel; and
      (ii) a binding member that specifically binds to fluorescently labeled analyte of the fluorescently labeled sample, wherein the binding member is contained in and/or on a surface of the particles and wherein the capillary channel has a defined height to particle ratio; and
   (c) imaging the first analyte specific capture domain comprising the adhered particles in the capillary channel to detect whether fluorescently labeled analyte is bound by the binding member of the particles and therefore present in the sample, wherein the imaging is performed without washing to remove unbound sample components prior to imaging.

2. The method according to claim 1, wherein the detecting is quantitative.

3. The method according to claim 1, wherein the detecting is qualitative.

4. The method according to claim 1, wherein the capillary channel has a height that is 50 fold greater or less than an average diameter of the particles.

5. The method according to claim 1, wherein the particles are beads.

6. The method according to claim 1, wherein the particles are cells.

7. The method according to claim 1, wherein the sample is a biological sample.

8. The method according to claim 1, wherein the biological sample is from a human.

9. The method according to claim 1, further comprising generating a diagnostic report based on whether the analyte is present in the sample.

10. The method according to claim 1, wherein the particles are associated with an upper surface of the capillary channel and the imaging is conducted from above the capillary channel.

11. The method according to claim 1, wherein the capillary channel comprises a second analyte specific capture domain on an inner surface of the capillary channel at a known location, wherein the second analyte specific capture domain comprises:
   (a) particles adhered to the surface of the capillary channel; and
   (b) a second binding member that specifically binds to the second analyte that is fluorescently labelled and present in the fluorescently labelled sample, wherein the second binding member is contained in and/or on a surface of the particles; and
   wherein the method further comprises imaging the second analyte specific capture domain comprising the adhered particles in the capillary channel to detect whether the second analyte that is fluorescently labelled is bound by the second binding member of the particles and therefore present in the sample.

12. The method according to claim 11, wherein the first and second analyte specific capture domains are located at different positions in the capillary channel.

13. The method according to claim 1, wherein the particles are adhered to the surface of the capillary channel by covalent bonding.

14. The method according to claim 1, wherein the particles are adhered to the surface of the capillary channel by treating the surface of the capillary channel with oxygen plasma to produce a plasma etched surface and depositing the particles on the plasma etched surface in a manner sufficient to stably associate the particles with the inner surface of the capillary channel to produce capture beads.

15. A kit comprising:
   a cartridge device having a capillary channel that comprises an analyte specific capture domain on an inner surface of the capillary channel at a known location, wherein the analyte specific capture domain comprises:
      (a) particles adhered to the surface of the capillary channel; and
      (b) a binding member that specifically binds to the analyte, wherein the binding member is contained in and/or on a surface of the particles and wherein the capillary channel has a defined height to particle ratio; and
   a fluorescent label that specifically binds to the analyte when the analyte is bound by the binding member.

* * * * *

UNITED STATES PATENT AND TRADEMARK OFFICE
CERTIFICATE OF CORRECTION

PATENT NO. : 9,523,682 B2
APPLICATION NO. : 14/237858
DATED : December 20, 2016
INVENTOR(S) : Huang et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 65 days.

Signed and Sealed this
Twenty-fifth Day of September, 2018

Andrei Iancu
*Director of the United States Patent and Trademark Office*